US009758569B2

(12) United States Patent
Raines et al.

(10) Patent No.: US 9,758,569 B2
(45) Date of Patent: Sep. 12, 2017

(54) COLLAGEN MIMICS

(75) Inventors: Ronald T. Raines, Madison, WI (US); Matthew D. Shoulders, Madison, WI (US); Jonathan A. Hodges, Raleigh, NC (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 2041 days.

(21) Appl. No.: 11/807,270

(22) Filed: May 25, 2007

(65) Prior Publication Data

US 2007/0275897 A1    Nov. 29, 2007

Related U.S. Application Data

(60) Provisional application No. 60/808,745, filed on May 26, 2006.

(51) Int. Cl.
*C07K 14/78* (2006.01)
*C07K 5/097* (2006.01)
*C07K 14/00* (2006.01)

(52) U.S. Cl.
CPC ............ *C07K 14/78* (2013.01); *C07K 5/0821* (2013.01); *C07K 14/001* (2013.01)

(58) Field of Classification Search
None
See application file for complete search history.

(56) References Cited

U.S. PATENT DOCUMENTS

| 5,973,112 | A | 10/1999 | Raines |
| 6,096,710 | A | 8/2000 | Goodman et al. |
| 6,329,506 | B1 | 12/2001 | Goodman et al. |
| 6,388,054 | B1* | 5/2002 | Stewart et al. ............... 530/314 |
| 7,122,521 | B2 | 10/2006 | Raines et al. |
| 2005/0004032 | A1* | 1/2005 | Raines et al. .................. 514/12 |

FOREIGN PATENT DOCUMENTS

| AU | 2003200660 | 9/2006 |
| EP | 1007568 | 7/1998 |
| JP | 2001514189 | 5/2010 |
| WO | WO 2005/000872 | 1/2005 |
| WO | 2007139914 | 12/2007 |

OTHER PUBLICATIONS

V. Nagarajan et al. J. Biochem. (1998) 124(6), pp. 1117-1123.*
J.J. Hutton Jr. et al. Arch. Biochem. Biophys. (1968) 125(3), pp. 779-785.*
DeRuiter ('Resonance and induction tutorial' retrieved from http://www.auburn.edu/~deruija/pdareson.pdf on May 24, 2013, 8 pages).*
Doi et al ('Characterization of collagen model peptides containing 4-fluoroproline' JACS v125 2003 pp. 9922-9923).*
Stage iiia lung cancer treatment'( retreived from http://coolessay.org/docs/index-248796.html on May 24, 2013, 4 pages).*
Tanaka et al ('A synthetic model of collagen structure taken from bovine macrophage scavenger receptor' FEBS Letters v334(3) Nov. 1993 pp. 272-276).*
Nevalainen et al ('Synthesis of Fmoc-Protected trans-4-methylproline' J Org Chem v66 2001 pp. 2061-2066).*
IUPAC Goldbook (definition for thiols retrieved from http://goldbook.iupac.org/T06359.html on Mar. 25, 2014, 1 page).*
Thiol definition (retrieved from http://chemistry.about.com/od/organicchemistryglossary/g/Thiol-Definition.htm on Mar. 25, 2014, 1 page).*
Kuwata et al ('Total synthesis of leucinostatin D' Tetrahedron letters 1992, abstract only retrieved from http://www.sciencedirect.com/science/article/pii/S0040403900609152 on Mar. 25, 2014, 2 pages).*
Koskinen et al ('Locked conformations for proline pyrrolidine ring: synthesis and conformational analysis of cis- and trans-4-tert-butylprolines' Journal of Organic Chemistry v70 2005 pp. 6447-6453).*
Jenkins, C.L., et al., "Insights on the conformational stability of collagen," Nat. Prod. Rep. 19:49-59 (2002).
Jones, E.Y., et al., "Analysis of Structural Design Features in Collagen," J. Mol. Biol. 218:209-219 (1991).
Koskinen, A.M.P., et al., "Locked Conformations for Proline Pyrrolidine Ring:Synthesis and Conformational Analysis of cis- and trans- . . . ," J. Org. Chem. 70:6447-6453 (2005).
Raines, Ronald T., "Award Address 2005 Emil Thomas Kaiser Award," Protein Sci. 15:1219-1225 (2006).
Sakakibara, S., et al., "Synthesis of (Pro-Hyp-Gly)n of defined molecular weights, Evidence for the Stabilization of Collagen Triple Helix . . . ," Biochimica et Biophysica Acta 303:198-202 (1973).
Shoulders, M.D., et al., "Reciprocity of Steric and Stereoelectronic Effects in the Collagen Triple Helix," JACS Communications.
U.S. Appl. No. 12/367,374, filed Feb. 6, 2009, Ronald T. Raines.
Eberhardt, E.S., et al., "Inductive Effects on the Energetics of Prolyl Peptide Bond Isomerization: Implications for Collagen . . . ," J. Am. Chem Soc. 118:12261-12266 (1996).
Hutton, J.J., et al., "Synthetic Polypeptides as Substrates and Inhibitors of Collagen Proline Hydroxylase," Archives of Biochemistry and Biophysics 125:779-785 (1968).
Kwak, J., et al., "Triple Helical Stabilities of Guest-Host Collagen Mimetic Structures," Bioorganic & Medicine Chemistry 7:153-160 (1999).
Takeuchi, T, et al., "Biosynthesis of Abnormal Collagens with Amino Acid Analogues," Biochimica et Biophysica Acta, 175:142-155 (1969).
O'Hagan, Understanding organofluorine chemistry. An introduction to the C—F bond, Chem Soc Rev. 2008; 37, 308-19. Epub Oct. 17, 2007.

(Continued)

*Primary Examiner* — Karlheinz R Skowronek
*Assistant Examiner* — Ronald Niebauer
(74) *Attorney, Agent, or Firm* — Quarles & Brady LLP

(57) ABSTRACT

Novel collagen mimics are disclosed with a tripeptide unit having the formula $(Xaa-Yaa-Gly)_n$, where one of the positions Xaa or Yaa is a bulky, non-electron withdrawing proline derivative. By substituting a proline derivative at either the Xaa or Yaa position in the native collagen helix, the stability of the helix is increased due solely to steric effects relative to prior known collagen-related triple helices. Methods are also disclosed for making the novel collagen mimics.

13 Claims, 10 Drawing Sheets

(56) References Cited

OTHER PUBLICATIONS

Becktel, W.J., et al., "Protein Stability Curves," Biopolymers 26:1859-1977 (1987).
Berg, R.A., et al., "The Thermal Transition of a Non-Hydroxylated Form of Collagen. Evidence for a Role . . . ," Biochem. and Biophys. Res. Comm. 52:115-120 (1973).
Bretscher, L.E., et al., "Conformational Stability of collagen Relies on a Stereoelectronic Effect," J. Am. Chem. Soc. 123:777-778 (2001).
Chopra, R.K., et al., "Conformational implications of enzymatic proline hydroxylation in collagen," Proc. natl. Acad. Sci. USA 79:7180-7184 (1982).
Del Valle, J.R., et al., "Asymmetric Hydrogenations for the Synthesis of Boc-Protected 4-Alkylprolinols and Prolines," J. Org. Chem. 68:3923-3931 (2003).
Engel, J., et al., "The Triple Helix—Coil Conversion of Collagen-Like Polytripeptides in Aqueous and Nonaqueous Solvents . . . ," Biopolymers 16:601-622 (1977).
Flippen-Anderson, J.L., et al., "Cyrstal Structures, Molecular Conformations, Infrared Spectra, and C NMR Spectra . . . ," J. Am. Chem. Soc. 105:6609-6614 (1983).
Gottlieb, A.A., et al., "Incorporation of cis- and trans-4-Fluoro-L-prolines into Proteins and Hydroxylation of the trans Isomer During . . . ," Biochemistry 4:25007-2513 (1965).
Hoeve, C.A., et al., "On the Structure of Water Absorbed in Collagen," J. Phys. Chem. 80:745-749 (1976).
Holmgren, S.K., et al., "A hyperstable collagen mimic," Chem. & Bio. 6:63-70 (1999).
Bella et al., "Crystal and Molecular Structure of a Collagen-Like Peptide at 1.9 A Resolution", Science (1994) 266:75-81.
Hodges, et al., "The Effect of Fluoroproline in the X-Position of the Stability of the Collagen Triple Helix", Abstract, Americal Peptide Symposium Jul. 23, 2003.
Panasik, et al., "Inductive effects on the structure of proline residues", Int. J. Peptide Protein Res. (1994) 44:262-269.
International Search Report dated Feb. 24, 2005 (International Patent Application No. PCT/US2004/020046, filed on Jun. 23, 2004).
International Preliminary Report on Patentability dated Jan. 3, 2006 (International Patent Application No. PCT/US2004/020046, filed on Jun. 23, 2004).
Written Opinion dated Dec. 23, 2005 (International Patent Application No. PCT/US2004/020046, filed on Jun. 23, 2004).
Office Action dated Jun. 3, 2008 (Japanese Patent Application No. 2000-507706, filed Jul. 9, 1998).
Office Action dated Jan. 5, 2009 (Japanese Patent Application No. 2000-507706, filed Jul. 9, 1998).
Uitto et al., Incorporation of Poline Analogs Into Procollagen: Assay for Replacement of Imino Acids by cis-4-Hydrox-L Proline and cis-4-Fluro-L-Proline, Archivees of Biochemistry and Biophysics 181, 293-299 (1977).
Examination Report dated Sep. 24, 2003 (European Patent Application No. 98935594.6, filed Jul. 9, 1998).
Examination Report dated Mar. 11, 2004 (European Patent Application No. 98935594.6, filed Jul. 9, 1998).
Examination Report dated Dec. 30, 2005 (European Patent Application No. 98935594.6, filed Jul. 9, 1998).
Office Action dated Oct. 4, 2006 (Canadian Patent Application No. 2,301,175, filed Jul. 9, 1998).
Office Action dated Sep. 7, 2007 (Canadian Patent Application No. 2,301,175, filed Jul. 9, 1998).
Office Action dated Apr. 30, 2009 (Canadian Patent Application No. 2,301,175, filed Jul. 9, 1998).
Examiner's Report dated May 25, 2001 (Australian Patent Application No. 2003200660, filed Feb. 25, 2003).
Examiner's Report dated Dec. 1, 2005 (Australian Patent Application No. 2003200660, filed Feb. 25, 2003).
Office Action dated May 16, 2006 (Australian Patent Application No. 2003200660, filed Feb. 25, 2003).
Office Action dated May 30, 2006 (U.S. Appl. No. 90/008,037, filed May 30, 2006).
Office Action with Decision Granting Petition; dated Feb. 12, 2007 (U.S. Appl. No. 90/008,037, filed May 30, 2005).
Office Action dated Jun. 28, 2007 (U.S. Appl. No. 90/008,037, filed May 30, 2005).
Office Action—Interview Summary; dated Feb. 12, 2007 (U.S. Appl. No. 90/008,037, filed May 30, 2005).
Office Action—Notice of Allowance; dated Nov. 3, 2010 (U.S. Appl. No. 12/367,374, filed Feb. 6, 2009).
Office Action—Notice of Allowance; dated Jun. 5, 2006 (U.S. Appl. No. 10/874,725, filed Jun. 23, 2004).
Holmgren, et al., Code for collagen's stability deciphered, Scientific Correspondence, Nature, vol. 392, Macmillan Publishers Ltd (1998).

\* cited by examiner

| Conformer | Energy | ZPVE | Energy (ZPVE-corrected) |
|---|---|---|---|
| mep endo | −632.642027277 | 0.238638 | −632.4033893 |
| mep exo | −632.640078157 | 0.238851 | −632.4012272 |
| Mep endo | −632.639069142 | 0.238857 | −632.4002121 |
| Mep exo | −632.641497308 | 0.238639 | −632.4028583 |

FIG. 7

COLLAGEN MIMICS

CROSS-REFERENCE TO RELATED APPLICATIONS

This application claims the benefit of U.S. Provisional Application No. 60/808,745 filed May 26, 2006. That application is incorporated herein by reference in its entirety.

STATEMENT REGARDING FEDERALLY SPONSORED RESEARCH OR DEVELOPMENT

This invention was made with government support under AR044276 awarded by the National Institutes of Health. The government has certain rights in the invention.

BACKGROUND

Collagen is the most abundant protein in vertebrates, occurring in virtually every tissue, including skin, tendon, bone, blood vessel, cartilage, ligament, and teeth. Collagen serves as the fundamental structural protein for vertebrate tissues. Collagen abnormalities are associated with a wide variety of human diseases, including arthritis, rheumatism, brittle bones, atherosclerosis, cirrhosis, and eye cataracts. Collagen is also critically important in wound healing. Increased understanding of the structure of collagen, and of how its structure affects its stability, facilitates the development of new treatments for collagen-related diseases and improved wound healing treatments.

Collagen is a fibrous protein consisting of three polypeptide chains that fold into a triple helix, Jenkins & Raines *Nat. Prod. Rep.,* 19:49-59 (2002). Mammals produce at least 17 distinct polypeptide chains that combine to form at least 10 variants of collagen. In each of these variants, the polypeptide chains of collagen are composed of approximately 300 repeats of the tripeptide sequence Xaa-Yaa-Gly, where Xaa is often a proline (Pro) residue and Yaa is often a 4(R)-hydroxyproline (Hyp) residue. In connective tissue (such as bone, tendon, cartilage, ligament, skin, blood vessels, and teeth), individual collagen molecules are wound together in tight triple helices. These helices are organized into fibrils of great tensile strength, Jones & Miller, *J. Mol. Biol.,* 218: 209-219 (1991). Varying the arrangements and cross linking of the collagen fibrils enables vertebrates to support stress in one-dimension (tendons), two-dimensions (skin), or three-dimensions (cartilage).

In vertebrates, the collagen polypeptide is translated with the typical repeat motif being ProProGly. Subsequently, in vivo, the hydroxylation of Pro residues is performed enzymatically after collagen biosynthesis but before the chains begin to form a triple helix. Thus, hydroxylation could be important for both collagen folding and collagen stability. The hydroxyl group of Hyp residues has long been known to increase the thermal stability of triple-helical collagen, Berg & Prockop, *Biochem. Biophys. Res. Comm.,* 52:115-120 (1973). For example, the melting temperature of a triple helix of (ProHypGly)$_{10}$ chains is 58° C., while that of a triple helix of (ProProGly)$_{10}$ chains is only 24° C., Sakakibara et al., *Biochem. Biophys. Acta,* 303:198-202 (1973). In addition, the rate at which (ProHypGly)$_{10}$ chains fold into a triple helix is substantially greater than the corresponding rate for (ProProGly)$_{10}$ chains, Chopra & Ananthanarayanan, *Proc. Natl. Acad. Sci. USA,* 79:7180-7184 (1982).

In general, molecular modeling based on the structure of triple-helical collagen and conformational energy calculations suggest that hydrogen bonds cannot form between the hydroxyl group of Hyp residues and any main chain groups of any of the collagen molecules in the same triple helix, Okuyama et al., *J. Mol. Biol.,* 152:247-443 (1981). Also, several models include the hypothesis that hydroxyproline increases the stability of collagen as a result of a bridge of water molecules formed between the hydroxyl group and a main chain carbonyl group. For reviews of observations advancing this hypothesis, see: Suzuki et al., *Int. J. Biol. Macromol.,* 2:54-56 (1980), and Némethy, in Collagen, published by CRC press (1988), and the references cited therein.

However, there exists experimental evidence that is inconsistent with the bridging the water molecule model. For example, the triple helices of (ProProGly)$_{10}$ and (ProHypGly)$_{10}$ were found to be stable in 1,2-propanediol, and Hyp residues conferred added stability in these anhydrous conditions, Engel et al., *Biopolymers,* 16:601-622 (1977), suggesting that water molecules do not play a part in the added stability of (ProHypGly)$_{10}$. In addition, heat capacity measurements are inconsistent with collagen having more than one bound water per six Xaa-Yaa-Gly units, Hoeve & Kakivaya, *J. Phys. Chem.,* 80:754-749 (1976). There exists no prior definitive demonstration of the mechanism by which the hydroxyproline residues stabilize collagen triplexes. Therefore, the molecular basis for these observed effects is still not clear. However, recent structural studies have begun to shed light on the structure and stability of collagen's triple-helix, see: Jenkins & Raines, *Nat. Prod. Rep.,* 19:49-59 (2002); and Raines, R. T. *Protein Sci.,* 15:1219-1225 (2006).

Further, it was previously shown that replacing Pro or Hyp in the Yaa position with (2S,4R)-4-fluoroproline (Flp), first synthesized by Gottleib et al., *Biochemistry,* 4:11:2507-2513 (1965), greatly increases triple helix stability, see: U.S. Pat. No. 5,973,112; Holmgren et al., *Nature,* 392:666-667 (1998); and Holmgren et al., *Chem. Biol.,* 6:63-70 (1999). In contrast, it has been shown that replacing Pro or Hyp in the Yaa position with the diastereomer (2S,4S)-4-fluoroproline (flp) greatly decreases stability, see: Bretscher et al., *J. Am. Chem. Soc.,* 123:777-778 (2001). Accordingly, it is believed that a better understanding of how the structure of collagen contributes to its stability would facilitate the design of a collagen or collagen mimics with improved stability.

A highly stable collagen substitute could advance the development of improved wound healing treatments. In recent years, there have been exciting developments in wound healing, including the development of tissue engineering and tissue welding. For example, autologous epidermal transplantation for the treatment of burns was a significant advance in tissue engineering. Tissue engineering has also led to the development of several types of artificial skin, some of which employ human collagen as a substrate. However, a major problem associated with this treatment is the fragile nature of these grafts during and after surgery.

Tissue welding is a wound healing technique in which a laser is used to thermally denature the collagen in the skin at the periphery of a wound. The wound is reannealed by permitting the renaturation of the collagen. In the case of large wounds, a "filler" or solder is required to effect reannealing of the wound. Various materials, including human albumin, have been used as solders for this purpose. A good solder is resilient and is non-immunogenic and should preferably be capable of interaction with native collagen in adjacent sites.

Collagen is also used for a variety of other medical purposes. For example, collagen is used in sutures which can be naturally degraded by the human body and thus do not have to be removed following recovery. A sometimes limiting factor in the design of collagen sutures is the strength of the collagen fibers. A collagen variant or mimic having a greater strength would aid in the usage of such collagen sutures by relieving this limitation. Accordingly, what is needed in the art is a novel collagen having increased stability for use in artificial skin, as a solder in tissue welding, and as a general tool for use in the design of medical constituents.

SUMMARY OF THE INVENTION

The present disclosure is summarized as novel variants of collagen, which have been designed to form a triple helix that is stronger than the native collagen. Specifically, collagen mimics are disclosed with a tripeptide unit having the formula $(Xaa-Yaa-Gly)_n$, where one of the positions Xaa or Yaa is a bulky, non-electron withdrawing proline derivative. By substituting a proline derivative at either the Xaa or Yaa position in the native collagen helix, the stability of the helix is increased due solely to steric effects relative to prior known collagen-related triple helices. Methods for making the novel collagen mimics are also described herein.

As such, a collagen mimic is disclosed having a tripeptide with the formula $(Xaa-Yaa-Gly)_n$. This is best illustrated using general structural configuration found in FIG. 1. In the Xaa position, R2 is H and R1 may be any bulky and non-electron withdrawing (or electron donating substituent). Suitable R1 substituents may include but are not limited to alkyl groups (methyl, ethyl, propyl, isopropyl or longer alkyls) and thiols groups; but, an electronegative atom such as N, O, F, Cl, or Br may not be installed directly on C4 of the proline ring. Likewise, in the Yaa position, R1 is H and R2 may include any bulky and non-electron withdrawing (or electron donating substituent). Suitable R2 substituents may include but are not limited to alkyl groups (methyl, ethyl, propyl, isopropyl or longer alkyls) and thiols groups; but, an electronegative atom such as N, O, F, Cl, or Br may not be installed directly on C4 of the proline ring. The n is a positive integer.

Notably, in terms of stereochemistry, Xaa is a trans 4-substituted proline and Yaa is a cis 4-substituted proline, wherein the substituted group is a group that enforces pyrrolidine ring pucker via steric effects resulting in a collagen triple helix that has increased stability relative to the native collagen helix.

In one aspect, novel variants which endow structural stability to collagen include a methyl proline group in one or both of the Xaa and Yaa position of the triple helical collagen tripeptide having the formula $(Xaa\ Yaa\ Gly)_n$. For example, in the Xaa position, (2S,4R)-4-methylproline, or mep, is used, and in the Yaa position, then (2S,4S)-4-methylproline, or Mep, is used. A tripeptide is present in the collagen as at least one out of every three triplex repeats in the collagen.

In a related aspect, a triple helix of collagen mimic molecules is disclosed in which each of the molecules in the helix has a tripeptide formula of $(flp-Yaa-Gly)_n$, where Yaa is (2S,4S)-4-methylproline, flp is (2S,4S)-4-fluoroproline, and n is a positive integer.

In a related aspect, a triple helix of collagen mimic molecules is disclosed in which each of the molecules in the helix has a tripeptide formula of $(Xaa-Flp-Gly)_n$, where Xaa is (2S,4R)-4-methylproline, and where Flp is (2S,4R)-4-fluoroproline, and n is a positive integer. Other suitable substitutes for Flp can also include, for example, acetyl modified hydroxyproline, mesyl modified hydroxyproline, and trifluoromethyl modified hydroxyproline.

In a related aspect, novel variants are disclosed which endow structural stability to collagen by having a thioproline group in one or both of the Xaa and Yaa position of the triple helical collagen tripeptide having the formula $(Xaa\ Yaa\ Gly)_n$. In the Xaa position, (2S,4R)-4-thioproline is used, and in the Yaa position, then (2S,4S)-4-thioproline is used.

In a related aspect, a triple helix of collagen mimic molecules is disclosed in which each of the molecules in the helix has a tripeptide formula of $(flp-Yaa-Gly)n$, where Yaa is (2S,4S)-4-thioproline, flp is (2S,4S)-4-fluoroproline, and n is a positive integer.

In a related aspect, a triple helix of collagen mimic molecules is disclosed in which each of the molecules in the helix has a tripeptide formula of $(Xaa-Flp-Gly)n$, where Xaa is (2S,4R)-4-thioproline, and where Flp is (2S,4R)-4-fluoroproline, and n is a positive integer. Other suitable substitutes for Flp can also include, for example, acetyl modified hydroxyproline, mesyl modified hydroxyproline, and trifluoromethyl modified hydroxyproline.

It is an object of the present invention to provide a novel, high stability collagen molecule that could be used as a component in artificial skin, as a solder in tissue welding, or as a substitute for collagen in other applications requiring high strength.

It is a feature of the present invention that evidence is provided to demonstrate the nature of the additional stability added to collagen by the proline residue, thereby making it possible to design other residues for that position which would increase that stability.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages, and features of the present invention will become apparent upon review of the specification, drawings, and claims.

DESCRIPTION OF THE DRAWINGS

FIG. 2A shows the spectra of peptide solutions (0.2 mM in 50 mM acetic acid) incubated at less than or equal to 4° C. for more than 24 h. FIG. 2B shows the effect of temperature on the molar ellipticity at 225 nm for (Pro-Mep-Gly)$_7$ and (mep-Mep-Gly)$_7$ or 227 nm for (mep-Pro-Gly)$_7$. Data were recorded at intervals of 1 or 3° C. after equilibration for at least 5 min.

FIG. 7 is a table showing self-consistent field energies of Ac-Yaa-OMe. SCF energies (atomic units; au) of Ac-Yaa-OMe is calculated with B3LYP at 6-311+G(2d,p).

DETAILED DESCRIPTION OF THE INVENTION

The investigation that led to the work described here began with the notion that a better understanding of the factors that contribute to the three dimensional structure and stability of collagen would facilitate the design of a collagen variant having improved strength for use in wound healing, and the development of treatments for people suffering from collagen-related illnesses. It would also provide a stronger, general purpose collagen for a variety of uses.

Steric and stereoelectronic effects play a defining role in molecular conformation and reactivity. In small molecules, steric and stereoelectronic effects often have dichotomous consequences. For example, the anomeric effect in glycosides yields axial substituents that are disfavored by steric interactions. Similarly, replacing the steric effect of a methyl group with the stereoelectronic effect of a fluoro group enables a β-peptide to fold. It has been shown before that stereoelectronic effects can be used to increase stability of collagen variants over the natural collagen form. Here we show that steric effects can be used to the same end.

In the native collagen polymer, the polyproline type II helices consist of over 300 repeats of the unit Xaa-Yaa-Gly, where Xaa is often S-proline (Pro) and the Yaa is often (2s,4r)-4-hydroxyproline (Hyp). The pyrrolidine ring in the Xaa and Yaa positions have complementary puckers preordained by a stereoelectronic effect. This stereoelectronic effect enhances the stability of collagen. One can achieve similar stereoelectronic effects substituting (2S,4S)-4-fluoroproline or "flp" for Xaa and (2S,4R)-4-fluoroproline or "Flp" for Yaa. Here we achieve that same level of stability using steric effects.

Figure 1:
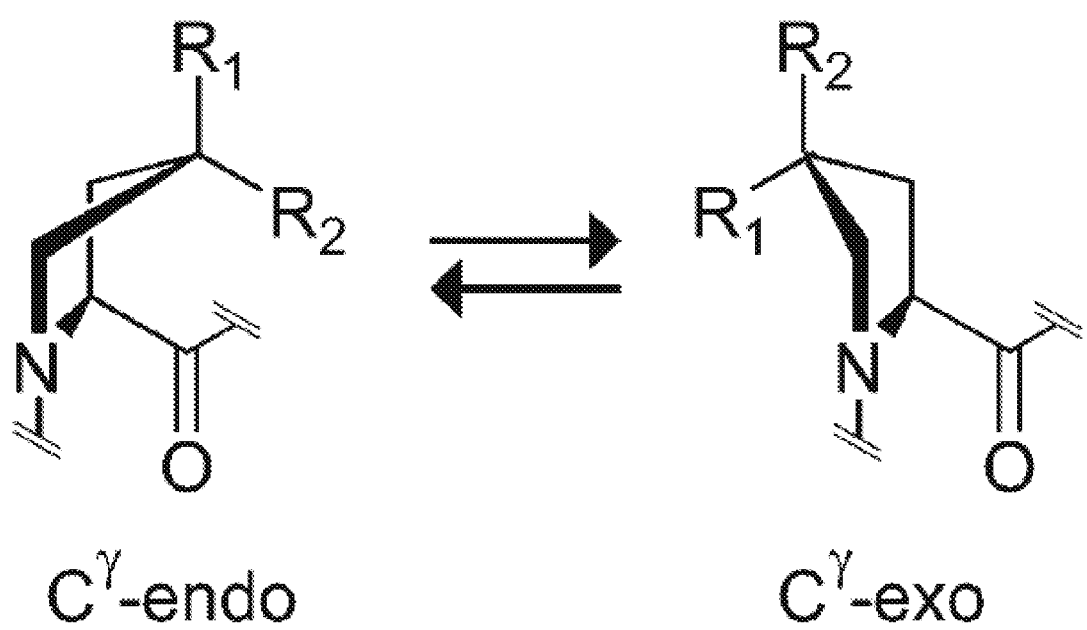
FIG. 1. illustrates the pucker of the proline variants described here and the ring conformations of 4-substituted proline residues. Suitable groups for the R1 and R2 positions are described in the detailed description below.

A broadly defined embodiment of the invention includes collagen mimics that contain one or more substitutions relative to the native collagen helix formed of repeats of the tripeptide motif Pro-Hyp-Gly. The metes and bounds of this embodiment can be readily illustrated using FIG. 1, which shows the pucker of the proline variants described here and the ring conformations of 4-substituted proline residues.

Accordingly, a collagen mimic is disclosed having a tripeptide with the formula (Xaa-Yaa-Gly)$_n$. In the Xaa position, R2 is H and R1 may be any bulky and non-electron withdrawing (or electron donating substituent). Suitable R1 substituents may include but are not limited to alkyl groups (methyl, ethyl, propyl, isopropyl or longer alkyls) and thiols groups; but, an electronegative atom (N, O, F, Cl, Br) may not be installed directly on C4 of the proline ring. Likewise, in the Yaa position, R1 is H and R2 may include any bulky and non-electron withdrawing (or electron donating substituent). Suitable R2 substituents may include but are not limited to alkyl groups (methyl, ethyl, propyl, isopropyl or longer alkyls) and thiols groups; but, an electronegative atom (N, O, F, Cl, Br) may not be installed directly on C4 of the proline ring. The n is a positive integer, suitably at least 3.

Notably, in one aspect of this embodiment, applicants identified that the pyrrolidine ring of (2S,4R)-4-methylproline (mep) has a strong preference for a pucker matching that of (2S,4S)-4-fluoroproline, while (2S,4S)-4-methylproline (or Mep) has a strong preference for a pucker matching that of (2S,4R)-4-fluoroproline. Specifically, according to FIG. 1, the Cγ-endo conformation is favored strongly by steric effects when R1=Me, R2=H (mep) or stereoelectronic effects when R1=H and R2=F (flp). Similarly, the Cγ-exo conformation is favored strongly by steric effects when R1=H, R2=CH3 (Mep) or stereoelectronic effects when R1=OH, R2=H (Hyp) or R1=F, R2=H (Flp). Thus, substituting one or both of mep and Mep into the appropriate positions in the collagen helix results in a collagen mimic of increased stability due solely to steric effects.

Accordingly, in one embodiment, collagen tripeptide mimics (Pro-Mep-Gly)$_7$, (mep-Pro-Gly)$_7$ and (mep-Mep-Gly)$_7$ are disclosed, which are more stable than the native form of collagen. In a related embodiment, the results obtained from these methylproline tripeptides were combined with applicants prior work (i.e., disclosing the use of (2S,4S)-4-fluoroproline (flp) in the first position and (2S,4R)-4-fluoroproline (Flp) in the second position) to discover that flp-Mep-Gly and mep-Flp-Gly offer similar advantages over natural collagen. In fact, the variants flp-Mep-Gly and mep-Flp-Gly exhibited higher melting temperatures that any of the other known collagen mimics.

Applicants note that not every variant in this motif yields structures with added stability. For example, a collagen mimic constructed with the motif flp-Flp-Gly turned out to yield relatively unstable collagen variants, even though the variants with the fluoroproline in only one position had improved stability. The explanation for this result seems to be steric hindrance between the fluorine atoms. The methyl groups in the methylproline variants taught here do not have the same problem as these groups are positioned extending (jut out) radially from the axis of the collagen tripeptide helix and hence they do not interfere with each other. As such, it is reasonable to expect that the methyl groups in the methylproline variants could be substituted by other alkyl or functional groups to achieve the same effect, in the same manner as the methyl groups.

In one embodiment, a thiol group can be substituted for a methyl group in the collagen tripeptide as sulfur is also a bulky electron donating substituent. A thiol group behaves like a methyl, as sulfur has a large size and a similar electronegativity to carbon. The sulfur of a thiol group, like the carbon of a methyl group, has only modest electronegativity (2.5 on the Pauling scale) and hence is expected to exert its effects by steric rather than stereoelectronic effects.

Accordingly, as used herein the abbreviation "thp" refers to (2S,4R)-thioproline. Similarly, (2S,4S)-thioproline can be abbreviated as "Thp". These thioprolines may be incorporated as an amino acid derivative into a collagen tripeptide to improve its stability relative to the native collagen tripeptide. Suitable tripeptides include, for example, (thp-Thp-Gly)$_7$, (thp-Mep-Gly)$_7$, (mep-Thp-Gly)$_7$, (Pro-Thp-Gly)$_7$, (thp-Pro-Gly)$_7$, (thp-Hyp-Gly)$_7$, (flp-Thp-Gly)$_7$, and (thp-Flp-Gly) 7.

It is also contemplated that the use of the steric and stereoelectronic effects can be combined. For example, one could install a proline at the first (Yaa) position with both a fluoro and a methyl group attached to the C4, with the fluoro group in the 4(R) configuration and the methyl group in the 4(S) configuration. Similar variants, with the appropriate configuration, can be envisioned at the Xaa position, again provided only that the variants which reduce stability (fluoro groups interfering between Xaa and Yaa) are avoided.

Thus, it is envisioned here that the mep and Mep containing collagen constituents can be used in collagen mimics with other proline derivatives at the other position. As used herein, the term "proline derivatives" is intended to include but is not limited to Hyp or (2S,4R)-4-hydroxyproline, flp or (2S,4S)-4-fluoroproline, Flp or (2S,4R)-4-fluoroproline, mep or (2S,4S)-4-methylproline or, Mep or (2S,4R)-4-methylproline, Thp or (2S,4R)-4-thioproline, thp or (2S,4S)-4-thioproline, and other longer alkyl proline derivatives described herein. Such proline derivatives are bulky in size and have a similar electronegativity as carbon, but are not prevented by steric hindrance from incorporation into a collagen triple helical strand.

As used herein, the term "alkyl proline derivatives" is intended to include but is not limited to derivatives of proline where the functional group is 4-methyl, 4-ethyl, 4-propyl, 4-isopropyl, and other perhaps longer alkyl groups with similar electron donating substituents. Suitable alkyl proline derivatives enforce ring pucker via the steric effect and should thus be stabilizing to collagen triple helices. Notably, the thiol groups are also encompassed within this functional definition, given that sulfur and carbon have similar electronegativities and that sulfur is much larger (bulkier) than carbon.

It is also envisioned that stronger collagen polymers can be made using the techniques described here even if the triplex motifs described here only make up a portion of the triplexes in the collagen monomers. For example, a collagen monomer could be Aaa-Baa-Gly-Xaa-Yaa-Gly-Aaa-Bbb-Gly, where Aaa is Pro, Baa is Mep, Xaa is Pro and Yaa is Hyp (or Flp). Or the Mep and Hyp could be reversed. It is envisioned that many such arrangements of triplex combinations are possible.

It is to be understood that this invention is not limited to the particular methodology, protocol, and reagents described, and as such may vary. It is also to be understood that the terminology used herein is for the purpose of describing particular embodiments only, and is not intended to limit the scope of the present invention which will be limited only by the appended claims.

EXAMPLES

Example 1: Experimental Materials and Methods

Commercial chemicals were of reagent grade or better, and were used without further purification. Anhydrous THF, DMF, and $CH_2Cl_2$ were obtained from CYCLE-TAINER® solvent delivery systems (J. T. Baker, Phillipsburg, N.J.). Other anhydrous solvents were obtained in septum-sealed bottles. In all reactions involving anhydrous solvents, glassware was either oven- or flame-dried. $NaHCO_3$ and brine (NaCl) refer to saturated aqueous solutions unless specified otherwise. Flash chromatography was performed with columns of silica gel 60, 230-400 mesh (Silicycle, Quebec City, Canada). Semi-preparative HPLC was performed with a Zorbax C-8 reversed-phase column. Analytical HPLC was performed with an Agilent C-8 reversed-phase column using linear gradients of solvent A ($H_2O$ with 0.1% v/v TFA) and solvent B ($CH_3CN$ with 0.1% v/v TFA).

The term "concentrated under reduced pressure" refers to the removal of solvents and other volatile materials using a rotary evaporator at water aspirator pressure (<20 torr) while maintaining the water-bath temperature below 40° C. Residual solvent was removed from samples at high vacuum (<0.1 torr). The term "high vacuum" refers to vacuum achieved by a mechanical belt-drive oil pump.

NMR spectra were acquired with a Bruker DMX-400 Avance spectrometer ($^1H$, 400 MHz; $^{13}C$, 100.6 MHz) at the National Magnetic Resonance Facility at Madison (NMR-FAM). NMR spectra were obtained at ambient temperatures on samples dissolved in $CDCl_3$ unless indicated otherwise. Coupling constants J are provided in Hertz. Compounds with a carbamate protecting group (e.g., Boc or Fmoc) exist as mixtures of Z and E isomers that do not interconvert on the NMR time scale at ambient temperatures. Accordingly, these compounds exhibit two sets of NMR signals, except when spectra are obtained at higher temperature (as indicated).

Mass spectrometry was performed with either a Micromass LCT (electrospray ionization, ESI) in the Mass Spectrometry Facility in the Department of Chemistry or an Applied Biosystems Voyager DE-Pro (matrix-assisted laser desorption/ionization, MALDI) mass spectrometer in the University of Wisconsin Biophysics Instrumentation Facility.

Example 2: Synthesis of N-tert-Butyloxycarbonyl-(2S,4R)-4-methylproline (1) and (S)-2-tert-butyldimethylsilyloxymethyl-N-tert-butyloxycarbonyl-4-methylenepyrrolidine (7)

Figure 3:
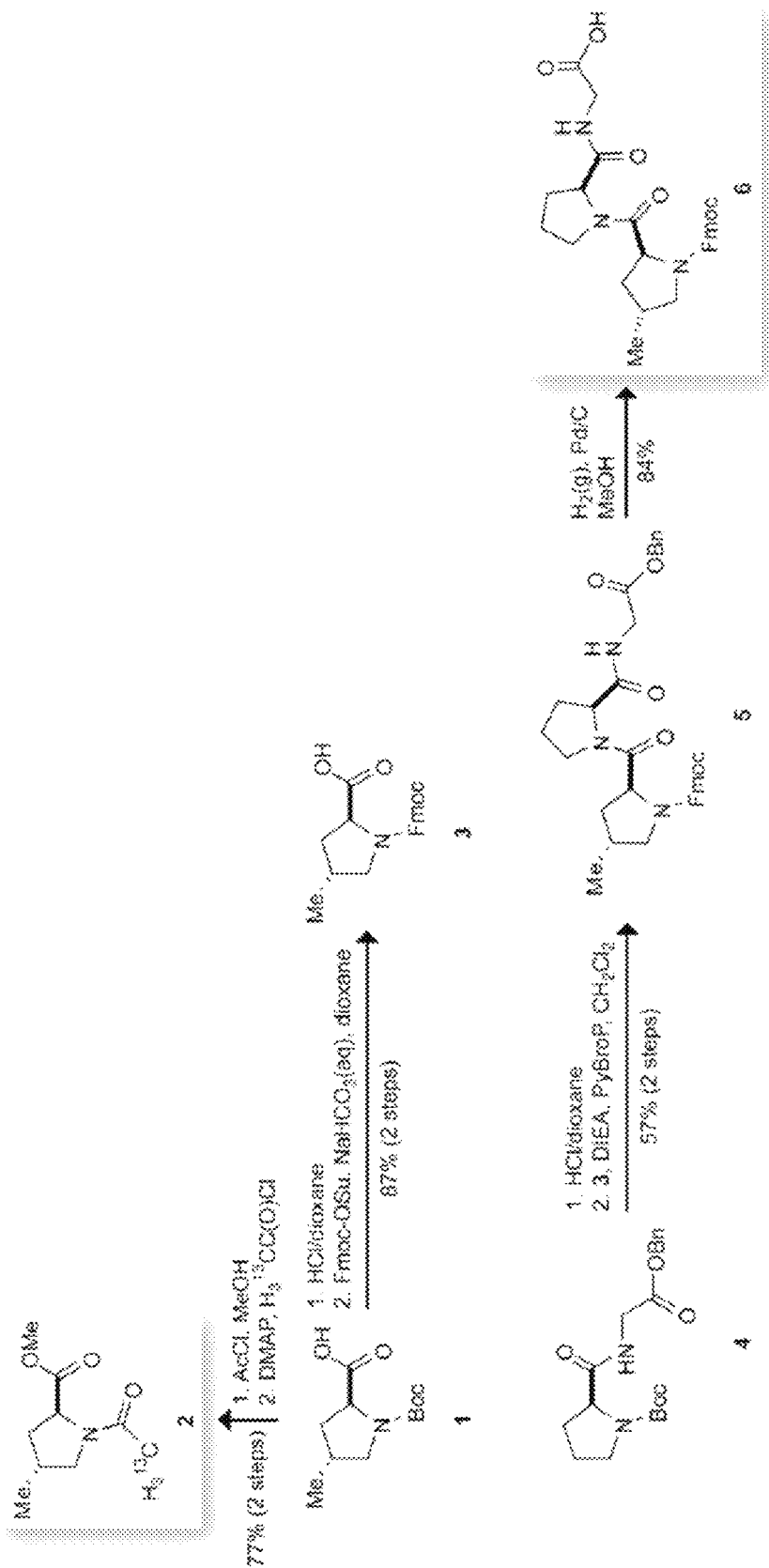
FIG. 3 shows a scheme for the synthesis of Fmoc-mep-Pro-GlyOH (6).
Figure 4:
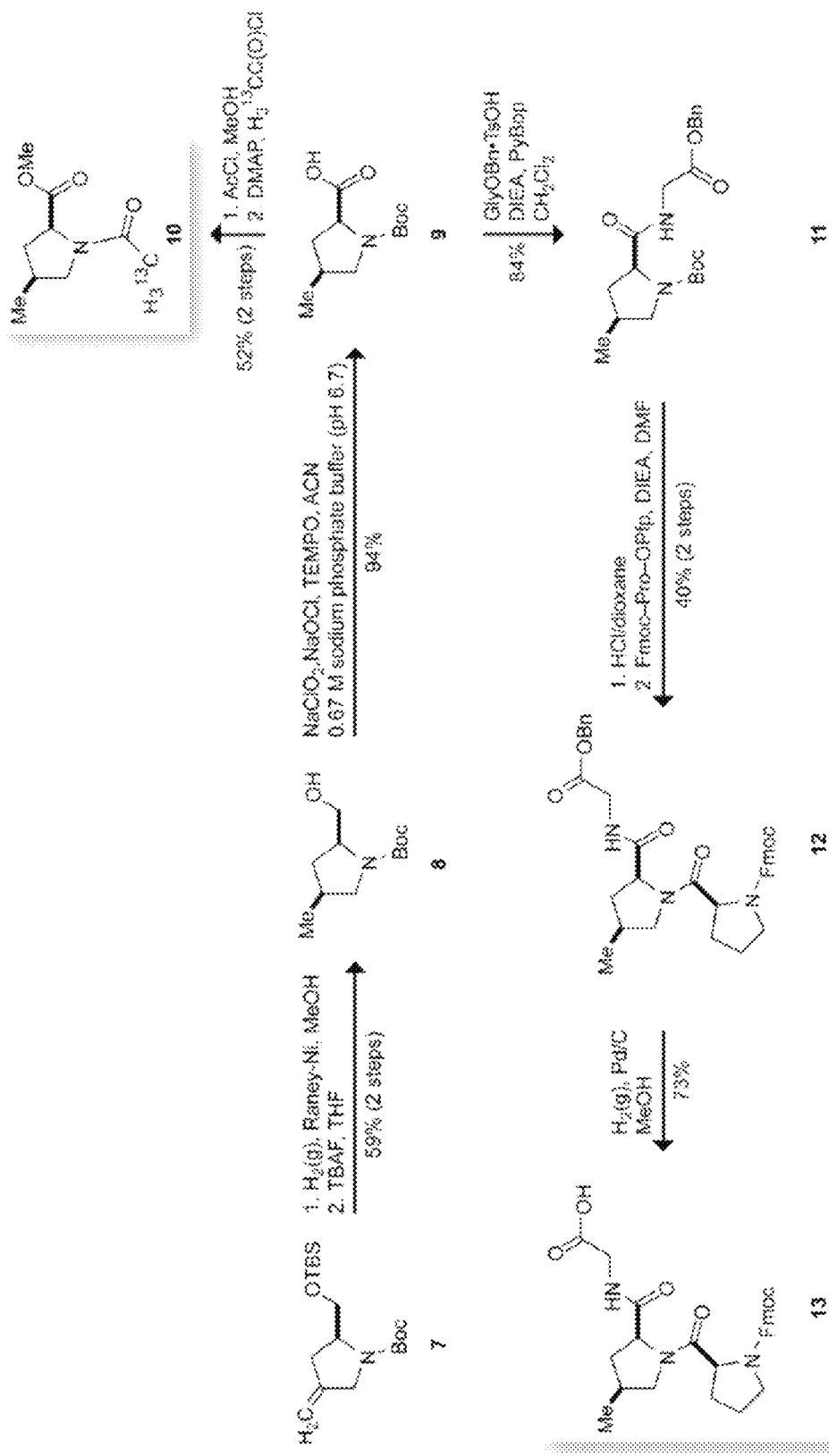
FIG. 4 shows a scheme for the synthesis of Fmoc-Pro-Mep-GlyOH (13).
Figure 5:
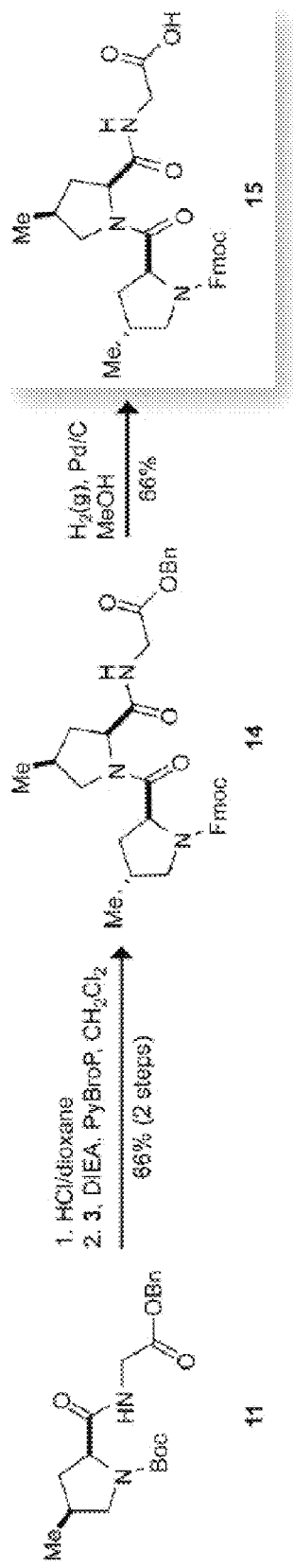
FIG. 5 shows a scheme for the synthesis of Fmoc-mep-Mep-GlyOH (15).
Figure 6:
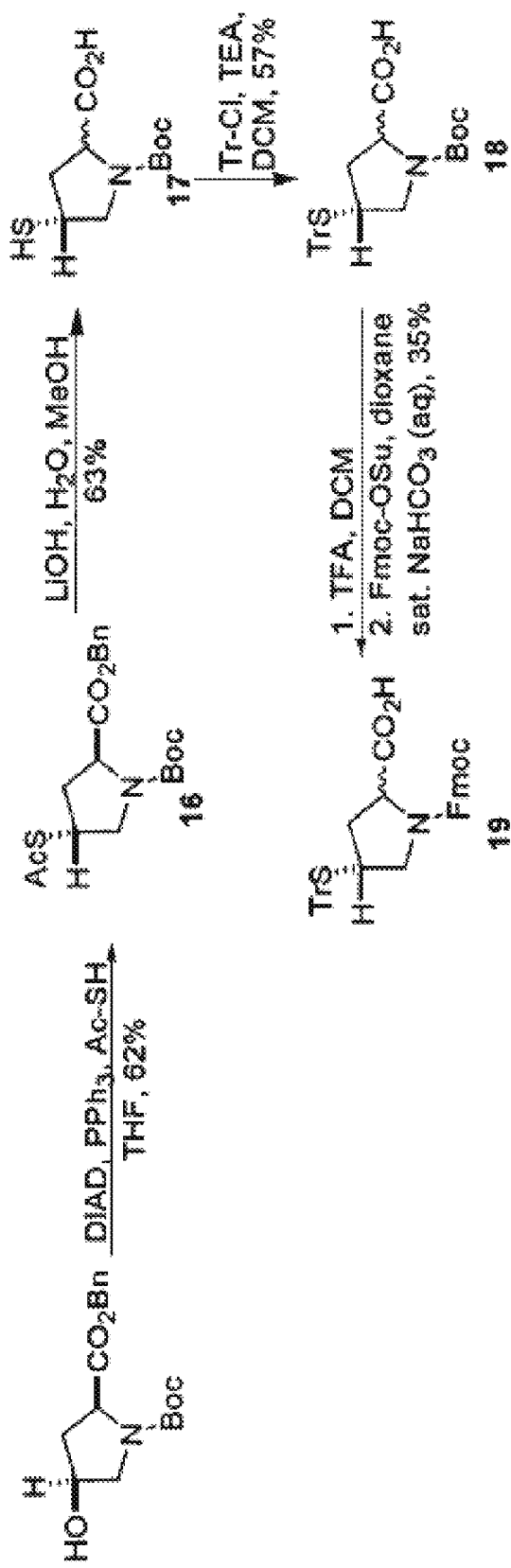
FIG. 6 shows a scheme for the synthesis of Fmoc-(2S, 4R)-thioproline (19), a thioproline derivative that can be used to incorporate thioprolines in collagen mimics via solid phase peptide synthesis in a manner analogous to that used to synthesize other collagen mimics described herein.

These compounds were synthesized by the method of Del Valle and Goodman M. *J. Org. Chem.* 2003, 68, 3923-3931. N-tert-Butyloxycarbonyl-S-prolyl-glycine benzyl ester (4) was synthesized by the method of Jenkins et al., *T. Org. Lett.* 2005, 7, 2619-2622. Synthetic routes to N-(9-fluorenylmethoxycarbonyl)-(2S,4R)-4-methylprolyl-S-prolyl-glycine 6 and N-(2-$^{13}CH_3$-acetyl)-(2S,4R)-4-methylproline methyl ester (2), N-(9-fluorenylmethoxycarbonyl)-(2S)-prolyl-(2S,4S)-4-methylprolyl-glycine (13) and N-(2-$^{13}CH_3$-acetyl)-(2S,4S)-4-methylproline methyl ester (10), and N-(9-fluorenylmethoxycarbonyl)-(2S,4R)-4-methylprolyl-(2S,4S)-4-methylprolyl-glycine (15) are summarized in FIGS. 3-5, respectively. The synthesis for compounds 16-19 are summarized in FIG. 6.

Example 3: Synthesis of N-(2-$^{13}CH_3$-Acetyl)-(2S, 4R)-4-methylproline methyl ester (2)

Following the method of Nudelman et al, *Synth. Commun.* 1998, 28, 471-474, compound 1 (80 mg, 0.35 mmol) was dissolved in anhydrous MeOH (11 mL), and the resulting solution was cooled to 0° C. Acetyl chloride (12.1 g, 150 mmol) was added dropwise and the reaction mixture was allowed to warm slowly to room temperature and stirred for 6 h. The resulting solution was concentrated under reduced pressure and the residue dissolved in anhydrous $CH_2Cl_2$ (15 mL). N,N-4-Dimethylaminopyridine (385 mg, 3.2 mmol)

was added, followed by the dropwise addition of $H_3^{13}CC(O)Cl$ (250 mg, 3.0 mmol) and the reaction mixture was stirred for 24 h. MeOH (5 mL) was added to quench the reaction. The resulting solution was concentrated under reduced pressure, and the residue was dissolved in 10% w/v aqueous citric acid, extracted with $CH_2Cl_2$ (2×40 mL), dried over anhydrous $MgSO_4(s)$, and concentrated under reduced pressure. The crude product was purified by flash chromatography (50% v/v EtOAc in hexane to elute byproducts followed by 6% v/v MeOH in EtOAc) to afford 2 (50 mg, 0.27 mmol, 77%) as a colorless oil. $^1H$ NMR δ: 1.08 and 1.07 (2 d, J=5.8, 3H), 1.76-1.86 (m, 1H), 2.08 (d, $J_{C-H}$=128, 3H), 2.06-2.09 (m, 1H), 2.52 (m, 1H), 3.05 (t, J=9.2, 1H), 3.71-3.83 (m, 4H), 4.41 and 4.54 (2 dd, J=2.4, 9.0, 1H); $^{13}C$ NMR δ: 17.5, 17.9, 22.1, 22.3, 32.7, 37.2, 52.4, 53.3, 54.9, 58.7, 60.7, 169.3, 169.8, 173.0; HRMS-ESI (m/z): $[M+Na]^+$ calcd for $C_8^{13}CH_{15}NO_3Na$, 209.0983; found, 209.0987.

Example 4: Synthesis of N-(9-Fluorenylmethoxycarbonyl)-(2S,4R)-4-methylproline (3)

Compound 1 (0.88 g, 3.8 mmol) was dissolved in 4 N HCl in dioxane (20 mL) under Ar(g) and stirred for 1.5 h. The resulting solution was concentrated under reduced pressure and the residue dissolved in dioxane and concentrated under reduced pressure again. The resulting free amine was dissolved in 10% w/v aqueous $NaHCO_3$ (55 mL), and a solution of Fmoc-OSu (1.41 g, 4.2 mmol) in dioxane (18 mL) was added. Additional dioxane (40 mL) was added, and the resulting white suspension stirred for 27 h. The dioxane was removed under reduced pressure and the aqueous solution was diluted with water (100 mL) and washed with ether (4×60 mL). The aqueous layer was acidified to pH 1.5 with 2 M HCl, extracted with EtOAc (4×160 mL), dried over anhydrous $MgSO_4(s)$, and concentrated under reduced pressure to afford 3 (1.11 g, 3.2 mmol, 87%) as a white solid. $^1H$ NMR δ: 1.04 and 1.08 (d, J=6.5, 3H), 1.73-1.94 (m, 1H), 2.11-2.20 and 2.31-2.50 (m, 2H), 2.97-3.05 (m, 1H), 3.68-3.79 (m, 1H), 4.11-4.52 (m, 4H), 7.24-7.45 (m, 4H), 7.51-7.63 (m, 2H), 7.68-7.81 (m, 2H); $^{13}C$ NMR δ: 17.3, 31.2, 32.4, 36.7, 38.7, 47.1, 47.3, 53.6, 53.8, 58.9, 59.8, 66.0, 67.5, 68.2, 120.1, 120.2, 125.0, 125.2, 125.2, 127.2, 127.2, 127.8, 127.9, 141.5, 143.8, 143.9, 156.4, 175.3, 177.8; ESI-MS (m/z): $[M-H]^-$ calcd for $C_{21}H_{20}NO_4Na$, 350.1; found, 350.6.

Example 5: Synthesis of N-9-Fluorenylmethoxycarbonyl)-(2S,4R)-4-methylprolyl-S-prolyl-glycine benzyl ester (5)

Compound 4 (1.34 g, 3.8 mmol) was dissolved in 4 N HCl in dioxane (27 mL) under Ar(g) and stirred for 1.4 h. The resulting solution was concentrated under reduced pressure and the residue was dissolved in anhydrous $CH_2Cl_2$ (30 mL) and cooled to 0° C. Compound 3 (430 mg, 1.3 mmol) was added to the solution, followed by PyBroP (606 mg, 1.3 mmol) and DIEA (1.26 g, 9.8 mmol). The reaction mixture was allowed to warm slowly to room temperature, stirred for 36 h, and then washed with 10% w/v aqueous citric acid (100 mL), $NaHCO_3$ (100 mL), water (100 mL), and brine (100 mL), dried over anhydrous $MgSO_4(s)$, and concentrated under reduced pressure. The crude product was purified by flash chromatography (gradient: 100% hexane to 100% EtOAc) to afford 5 (442 mg, 0.7 mmol, 57%) as a white solid containing an unidentified impurity which was removed after the succeeding step. HRMS-ESI (m/z): $[M+Na]^+$ calcd for $C_{35}H_{37}N_3O_6Na$, 618.2580; found, 618.2594.

Example 6: Synthesis of N-9-Fluorenylmethoxycarbonyl-(2S,4R)-4-methylprolyl-S-prolyl-glycine (6)

MeOH (50 mL) was added carefully to a mixture of compound 5 (420 mg, 0.7 mmol) and Pd/C (10% w/w, 90 mg, 0.1 mmol) under Ar(g), and the resulting black suspension was stirred under $H_2(g)$ for 5 h. Careful monitoring by TLC was necessary to prevent hydrogenolysis of the Fmoc group. The suspension was filtered through a pad of Celite and concentrated under reduced pressure. The crude product was purified by flash chromatography (EtOAc to elute byproducts, then 25% v/v MeOH in $CH_2Cl_2$ with 0.1% formic acid). The fractions containing 6 were concentrated under reduced pressure, and the formic acid was removed by dissolving the residue in 10% v/v MeOH in toluene and concentrating under reduced pressure to afford 6 (300 mg, 0.6 mmol, 84%) as a white solid. The purity of 6 was determined to be 90% by analytical HPLC (gradient: 15% B to 85% B over 50 min). A small sample was purified further by semi-preparative HPLC for use in NMR experiments. $^1H$ NMR (spectrum obtained at 343 K in DMSO-$d_6$) δ: 1.06-0.93 (m, 3H), 1.7-2.47 (m, 7H), 2.81-3.75 (m, 6H), 4.11-4.58 (m, 5H), 7.26-7.46 (m, 4H), 7.50-7.92 (m, 5H); $^{13}C$ NMR (DMSO-$d_6$) δ: 17.4, 17.5, 24.3, 24.3, 28.9, 29.0, 30.0, 31.3, 36.3, 37.2, 46.1, 46.5, 46.6, 46.9, 53.1, 53.7, 57.6, 58.0, 59.1, 59.2, 66.0, 66.5, 120.0, 120.1, 124.8, 124.9, 125.1, 127.1, 127.2, 127.6, 127.7, 140.7, 143.9, 144.0, 153.6, 153.8, 158.1, 158.4, 158.8, 169.9, 170.0, 171.2, 171.8, 172.0; HRMS-ESI (m/z): $[M+Na]^+$ calcd for $C_{28}H_{31}N_3O_6Na$, 528.2111; found, 528.2108.

Example 7: Synthesis of N-tert-Butyloxycarbonyl-(2S,4S)-2-hydroxymethyl-4-methylpyrrolidine (8)

Following the method of Del Valle and Goodman, a 0.1 M solution of compound 7 (9.78 g, 29.8 mmol) in MeOH was prepared. Raney-nickel (~1.00 g) that had been washed repeatedly with MeOH was added to the solution, and the flask was flushed repeatedly with $H_2(g)$. The solution was stirred under $H_2(g)$ for 30 h and then filtered through a Celite pad. (Caution: do not Allow the Filter Cake to Dry During Filtration as Raney-Nickel can Rapidly Ignite.) The resulting solution was concentrated under reduced pressure and then dissolved in 0.5 M TBAF in THF (120 mL). After stirring for 15 h, the solution was concentrated under reduced pressure. The synthetic procedure was expected to yield both 8 and its trans diastereomer in a 3:1 ratio. The major diastereomer 8 was purified by flash chromatography (7% v/v EtOAc in hexane). Compound 8 was obtained (3.82 g, 17.7 mmol, 59% (2 steps)) as a colorless oil. The ratio of 8 to its 4R diastereomer was determined to be 30:1 by gas chromatography with a Supelco β-Dex-250 chiral column (17 m) and $N_2$ as the carrier gas at a column temperature of 110° C. $^1H$ NMR δ: 1.02 (d, J 6.1, 3H), 1.08 (m, 1H), 1.47 (s, 9H), 2.04-2.21 (m, 2H), 2.77 (t, J=10.1, 1H), 3.53-3.73 (m, 3H), 3.82-3.98 (m, 1H), 5.33 (d, J=8.4, 1H); $^{13}C$ NMR δ: 17.0, 28.5, 28.7, 37.5, 54.5, 55.0, 61.6, 67.9, 80.4, 157.1; ESI-MS (m/z): $[M+Na]^+$ calcd for $C_{11}H_{21}NO_3Na$, 238.1; found, 238.3.

Example 8: Synthesis of N-tert-Butyloxycarbonyl-(2S,4S)-4-methylproline (9)

Following the method of Del Valle and Goodman, three solutions were prepared prior to the oxidation. The first solution consisted of NaClO$_2$ (1.33 g, 14.7 mmol) in water (7.4 mL). The second solution consisted of bleach (436 μL) in water (7.4 mL). The third solution consisted of compound 8 (1.60 g, 7.4 mmol) dissolved in 100 mL of 3:2 CH$_3$CN:NaH$_2$PO$_4$ buffer (pH 6.6, 0.67 M). The solution containing 8 was heated to 45° C., and TEMPO (193 mg, 0.7 mmol) was added. The two oxidant solutions were added simultaneously in 618 μL portions over 1 h, and the resulting solution was stirred at 40° C. for 18 h. After cooling to room temperature, the reaction was quenched by dropwise addition of saturated aqueous Na$_2$SO$_3$ until the solution became colorless. The acetonitrile was removed under reduced pressure, and the resulting aqueous solution basified to pH 10 with 1 M NaOH. The basic solution was washed with ether (5×125 mL) and then acidified to pH 2 with 2 M HCl. The acidic solution was extracted with ether (4×200 mL), and the organic layer was dried over anhydrous MgSO$_4$(s) and concentrated under reduced pressure to afford 9 (1.60 g, 7.0 mmol, 94%) as a white solid. $^1$H NMR δ: 1.09 (d, J=6.0, 3H), 1.44 and 1.50 (s, 9H), 1.58-1.70 and 1.88-2.00 (m, 1H), 2.21-2.31 (m, 1H), 2.31-2.52 (m, 1H), 2.89-3.04 (m, 1H), 3.67-3.82 (m, 1H), 4.20-4.38 (2m, 1H); $^{13}$C NMR δ: 16.9, 17.2, 28.2, 28.3, 32.7, 36.4, 38.8, 53.3, 54.1, 59.4, 59.5, 80.4, 81.6, 159.4, 162.1, 174.9, 179.6; ESI-MS (m/z): [M−H]$^-$ calcd for C$_{11}$H$_{18}$NO$_4$, 228.1; found, 228.4.

Example 9: Synthesis of N-(2-$^{13}$CH$_3$-Acetyl)-(2S,4S)-4-methylproline methyl ester (10)

Following the method of Nudelman et al., compound 9 (100 mg, 0.44 mmol) was dissolved in anhydrous MeOH (10 mL), and the resulting solution was cooled to 0° C. Acetyl chloride (11.80 g, 150 mmol) was added dropwise and the reaction mixture was allowed to warm slowly to room temperature and stirred for 10 h. The resulting solution was concentrated under reduced pressure and the residue dissolved in anhydrous CH$_2$Cl$_2$ (15 mL). N,N-4-Dimethylaminopyridine (450 mg, 3.7 mmol) was added, followed by the dropwise addition of H$_3$$^{13}$CC(O)Cl (99 mg, 1.2 mmol). The reaction mixture was stirred for 9 h. Additional unlabeled acetyl chloride was added to ensure complete reaction, followed by MeOH (10 mL) to quench the reaction. The resulting solution was concentrated under reduced pressure, and the residue was dissolved in 10% w/v aqueous citric acid, extracted with CH$_2$Cl$_2$ (2×40 mL), dried over anhydrous MgSO$_4$(s), and concentrated under reduced pressure. The crude product was purified by flash chromatography (50% v/v EtOAc in hexane to elute byproducts followed by 6% v/v MeOH in EtOAc) to afford 10 (40 mg, 0.21 mmol, 52%) as a yellow oil. $^1$H NMR δ: 1.06 and 1.10 (2 d, J=6.4, 3H), 1.56 (q, J=10.5, 1H), 2.09 (d, J$_{C-H}$=128, 3H), 2.28-2.46 (m, 2H), 3.18 (t, J=9.8, 1H), 3.69 (m, 1H), 3.74 and 3.78 (2 s, 3H), 4.36 (t, J=8.4, 1H); $^{13}$C NMR δ: 17.0, 21.8, 22.4, 33.9, 37.6, 52.3, 55.1, 59.3, 168.9, 169.4, 173.1, 173.2; HRMS-ESI (m/z): [M+Na]$^+$ calcd for C$_8$$^{13}$CH$_{15}$NO$_3$Na, 209.0983; found, 209.0980.

Example 10: Synthesis of N-tert-Butyloxycarbonyl-(2S,4S)-4-methylprolyl-glycine benzyl ester (11)

Compound 9 (1.6 g, 7.0 mmol), glycine benzyl ester tosylate (3.07 g, 9.1 mmol), and PyBOP (3.64 g, 7.0 mmol) were dissolved in anhydrous CH$_2$Cl$_2$ (80 mL). DIEA (2.26 g, 17.5 mmol) was added, and the resulting solution was stirred for 27 h under Ar(g). The reaction mixture was washed with 10% w/v aqueous citric acid (3×50 mL), NaHCO$_3$ (3×50 mL), water (50 mL), and brine (50 mL), dried over anhydrous MgSO$_4$(s), and concentrated under reduced pressure. The crude oil was purified by flash chromatography (1:1 EtOAc:hexane) to afford 11 (2.13 g, 5.9 mmol, 84%) as a colorless, sticky liquid. $^1$H NMR δ: 1.03 and 1.04 (d, J=3.2, 3H), 1.44 (bs, 9H), 1.55-2.50 (m, 4H), 2.90 (t, J=9.8, 1H), 3.65-3.94 (m, 1H), 4.01-4.34 (m, 3H), 5.18 (s, 2H), 7.36 (bs, 5H); HRMS-ESI (m/z): [M+Na]$^+$ calcd for C$_{20}$H$_{28}$N$_2$O$_5$Na, 399.1896; found, 399.1897.

Example 11: Synthesis of N-9-Fluorenylmethoxycarbonyl-S-prolyl-(2S,4S)-4-methylprolyl-glycine benzyl ester (12)

Compound 11 (1.18 g, 3.3 mmol) was dissolved in 4 N HCl in dioxane (30 mL) under Ar(g) and stirred for 2.5 h. The resulting solution was concentrated under reduced pressure and the residue dissolved in anhydrous DMF (50 mL). DIEA (1.60 g, 12.2 mmol) was added, followed by Fmoc-Pro-OPfp (3.52 g, 7.0 mmol), and additional anhydrous DMF (20 mL). The solution was stirred for 48 h and then concentrated by rotary evaporation under high vacuum. Flash chromatography (gradient: 25% v/v EtOAc in hexane to 95% v/v EtOAc in hexane) afforded 12 (800 mg, 1.3 mmol, 40%) as a white solid. $^1$H NMR δ: 1.04 and 1.07 (d, J=6.5, 3H), 1.76-2.60 (m, 8H), 3.44-3.75 (m, 2H), 3.91-4.61 (m, 8H), 5.27 (s, 2H), 7.04-7.79 (m, 13H); HRMS-ESI (m/z): [M+Na]$^+$ calcd for C$_{35}$H$_{37}$N$_3$O$_6$Na, 618.2580; found, 618.2558.

Example 12: N-9-Fluorenylmethoxycarbonyl-S-prolyl-(2S,4S)-4-methylprolyl-glycine (13)

MeOH (130 mL) was added carefully to a mixture of compound 12 (800 mg, 1.3 mmol) and Pd/C (10% w/w, 160 mg, 0.2 mmol) under Ar(g), and the resulting black suspension was stirred under H$_2$(g) for 2 h. Careful monitoring by TLC was necessary to prevent hydrogenolysis of the Fmoc group. The suspension was filtered through a pad of Celite and concentrated under reduced pressure. The crude product was purified by flash chromatography (EtOAc to elute byproducts, then 12% v/v MeOH in CH$_2$Cl$_2$ containing 0.1% v/v formic acid). The fractions containing 13 were concentrated under reduced pressure and the formic acid was removed by dissolving the residue in 10% v/v MeOH in toluene and concentrating under reduced pressure to afford 13 (500 mg, 1.0 mmol, 73%) as a white solid. The purity of 13 was determined to be 90% by analytical HPLC (gradient: 15% B to 85% B over 50 min). $^1$H NMR (spectrum obtained at 343 K in DMSO-d$_6$) δ: 1.02 (d, J=6.5, 3H), 1.37-1.49 (m, 1H). 1.70-2.00 (m, 3H), 2.06-2.27 (m, 2H), 2.87-3.46 (m, 6H), 3.74-4.02 (m, 3H), 4.11-4.57 (m, 5H), 7.25-7.90 (m, 8H); $^{13}$C NMR (DMSO-d$_6$) δ: 16.8, 22.6, 23.7, 28.5, 29.3, 33.3, 33.4, 37.0, 37.1, 40.7, 46.2, 46.6, 46.8, 46.9, 53.6, 53.8, 57.6, 58.0, 59.8, 59.9, 66.3, 66.5, 120.1, 120.2, 125.0, 125.1, 125.1, 125.3, 127.1, 127.1, 127.2, 127.3, 127.7, 140.7, 140.7, 143.8, 143.9, 144.0, 153.8, 153.8, 169.5, 169.6, 171.2, 171.7, 171.7; HRMS-ESI (m/z): [M−H]$^-$ calcd for C$_{28}$H$_{30}$N$_3$O$_6$, 504.2135; found, 504.2121.

Example 13: Synthesis of N-9-Fluorenylmethoxycarbonyl-(2S,4R)-4-methylprolyl-(2S,4S)-4-methylprolyl-glycine benzyl ester (14)

Compound 11 (980 mg, 2.7 mmol) was dissolved in 4 N HCl in dioxane (30 mL) under Ar(g) and stirred for 1.7 h. The reaction mixture was concentrated under reduced pressure and the residue was dissolved in anhydrous CH$_2$Cl$_2$ (80 mL) and cooled to 0° C. Compound 3 (430 mg, 1.3 mmol) was added to the solution, followed by PyBroP (653 mg, 1.4 mmol) and DIEA (1.00 g, 7.8 mmol). The resulting solution was allowed to warm slowly to room temperature and then stirred for 40 h. The reaction mixture was diluted with $CH_2Cl_2$ (125 mL), washed with 10% w/v aqueous citric acid (100 mL), $NaHCO_3$ (100 mL), water (100 mL), and brine (100 mL), dried over anhydrous $MgSO_4$(s), and concentrated under reduced pressure. Flash chromatography (gradient: 35% v/v EtOAc in hexane to 90% v/v EtOAc in hexane) afforded 14 (520 mg, 0.9 mmol, 66%) as a white solid. $^1$H NMR δ: 0.96-1.30 (m, 6H), 1.63-3.13 (m, 9H), 3.69-4.66 (m, 7H), 5.15 (m, 2H), 7.14-7.79 (m, 13H); HRMS-ESI (m/z): [M+Na]$^+$ calcd for $C_{36}H_{39}N_3O_6Na$, 632.2737; found, 632.2712.

Example 14: Synthesis of N-9-Fluorenylmethoxy-carbonyl-(2S,4R)-4-methylprolyl-(2S,4S)-4-methyl-prolyl-glycine (15)

MeOH (60 mL) was added carefully to a mixture of compound 14 (520 mg, 0.9 mmol) and Pd/C (10% w/w, 160 mg, 0.2 mmol) under Ar(g), and the resulting black suspension was stirred under a hydrogen atmosphere for 2.5 h. Careful monitoring by TLC was necessary to prevent hydrogenolysis of the Fmoc group. The suspension was filtered through a pad of Celite and concentrated under reduced pressure. The crude product was purified by flash chromatography (EtOAc to elute byproducts, then 12% v/v MeOH in $CH_2Cl_2$ with 0.1% formic acid). The fractions containing 15 were concentrated under reduced pressure, and the formic acid was removed by dissolving the residue in 10% v/v MeOH in toluene and concentrating under reduced pressure to afford 15 (315 mg, 0.6 mmol, 66%) as a white solid. The purity of 15 was determined to be 90% by analytical HPLC (gradient 15% B to 85% B over 50 min). $^1$H NMR (spectrum obtained at 343 K in DMSO-$d_6$) δ: 0.9-1.05 (m, 6H), 1.27 (m, 1H), 1.42 (m, 1H), 1.72-1.82 (m, 1H), 2.01-2.35 (m, 4H), 2.84-3.00 (m, 3H), 3.48-3.66 (m, 3H), 3.70-3.80 (m, 1H), 4.23-4.59 (m, 4H), 7.29-7.45 (m, 4H), 7.52-7.77 (m, 2H), 7.84-7.91 (m, 2H); $^{13}$C NMR (DMSO-$d_6$) δ: 14.0, 16.8, 17.3, 17.5, 17.6, 18.2, 22.1, 30.0, 30.5, 31.0, 31.2, 31.2, 33.3, 33.4, 33.8, 35.3, 36.1, 37.0, 46.6, 47.0, 51.3, 51.6, 53.0, 53.6, 53.8, 57.9, 58.1, 58.4, 59.8, 59.9, 60.0, 66.2, 66.5, 109.6, 120.1, 120.2, 121.4, 124.9, 125.1, 125.1, 127.1, 127.1, 127.2, 127.3, 127.7, 127.7, 128.9, 140.7, 140.7, 143.8, 152.4, 153.8, 169.4, 169.5, 171.3, 171.5, 171.6; HRMS-ESI (m/z): [M−H]$^-$ calcd for $C_{29}H_{33}N_3O_6$, 518.2291; found, 518.2307.

Example 15: Measurement of $K_{trans/cis}$ Values of (2) and (10)

Each compound (5-10 mg) was dissolved in $D_2O$ with enough $CD_3OD$ added to solubilize the compound (less than 20% of total volume). The $^{13}$C NMR spectra were recorded using an inverse gated decoupling pulse program with a relaxation delay of 100 s and a pulse width of 10 μs. The spectral baselines were corrected and peaks corresponding to the labeled carbon were integrated with the software package NUTS-NMR Utility Transform Software, Acorn NMR, Inc., 7670 Las Positas Road, Livermore, Calif. 94551. Values of $K_{trans/cis}$ were determined by the relative areas of the trans and cis peaks for the labeled carbons.

Example 16: Attachment of Fmoc-mep-Pro-GlyOH (6) to 2-Chlorotrityl Resin

Under Ar(g), 33 mg (0.053 mmol) of 2-chlorotrityl resin (loading: 1.6 mmol/g) was swelled in anhydrous $CH_2Cl_2$ (0.7 mL) for 5 min. A solution of compound 6 (25 mg, 0.050 mmol) and DIEA (26 mg, 0.20 mmol) in anhydrous $CH_2Cl_2$ (0.7 mL) was added by syringe. Additional anhydrous $CH_2Cl_2$ (0.5 mL) was used to ensure complete transfer of 6. After 2 h, anhydrous MeOH (0.2 mL) was added to cap any remaining active sites on the resin. The resin-bound peptide was isolated by gravity filtration, washed with several portions of anhydrous $CH_2Cl_2$ (~25 mL), and dried under high vacuum. The mass of the resin-bound peptide was 57 mg. Loading was measured by ultraviolet spectroscopy to be 0.69 mmol/g (see, Applied Biosystems Determination of the Amino Acid Substitution Level via an Fmoc Assay; Technical Note 123485 Rev 2; Documents on Demand-Applied Biosystems Web Page, http://docs.appliedbiosystems.com/search.taf (Nov. 30, 2005)).

Example 17: Attachment of Fmoc-Pro-Mep-GlyOH (13) and Fmoc-mep Mep-GlyOH (15) to 2-Chlorotrityl Resin Fmoc-tripeptides 13 and 15 were loaded onto 2-chlorotrityl resin in similar fashion to that described for 6. Loadings were measured by ultraviolet spectroscopy[55] to be 0.56 mmol/g for 13 and 0.60 mmol/g for 15.

Example 18: Synthesis of (mep-Pro-Gly)$_7$, (Pro-Mep-Gly)$_7$, and (mep-Mep-Gly)$_7$ These three 21-mer peptides were synthesized by segment condensation of their corresponding Fmoc-tripeptides (6, 13, and 15) on solid phase using an Applied Biosystems Synergy 432A Peptide Synthesizer at the University of Wisconsin-Madison Biotechnology Center. The first trimer was loaded onto the resin as described above. Fmoc-deprotection was achieved by treatment with 20% (v/v) piperidine in DMF. The trimers (3 equivalents) were converted to active esters by treatment with HBTU, DIEA, and HOBt. Extended couplings (120-200 min) were employed at room temperature.

Peptides were cleaved from the resin in 95:3:2 TFA:triisopropylsilane:$H_2O$ (1.5 mL), precipitated from t-butylmethylether at 0° C., and isolated by centrifugation. Semipreparative HPLC was used to purify the peptides (mep-Pro-Gly)$_7$ (gradient: 10% B to 40% B over 50 min), (Pro-Mep-Gly)$_7$ (gradient: 15% B to 50% B over 50 min), and (mep-Mep-Gly)$_7$ (gradient: 15% B to 60% B over 60 min). All three peptides were >90% pure by analytical HPLC and MALDI-TOF mass spectrometry (m/z) [M+H]$^+$ calcd for $C_{91}H_{136}N_{21}O_{22}$ 1876.2. found 1875.6 for (mep-Pro-Gly)$_7$, 1875.4 for (Pro-Mep-Gly)$_7$. calcd for $C_{98}H_{150}N_{21}O_{22}$ 1974.4. found 1973.7 for (mep-Mep-Gly)$_7$.

Example 19: Circular Dichroism Spectroscopy of (mep-Pro-Gly)$_7$, (Pro-Mep-Gly)$_7$, and (mep-Mep-Gly)$_7$ Peptides were dried under vacuum for at least 24 h before being weighed and dissolved to 0.2 mM in 50 mM acetic acid (pH 2.9). The solutions were incubated at <4° C. for >24 h before CD spectra were acquired using an Aviv 202SF spectrometer at the University of Wisconsin Biophysics Instrumentation Facility. Spectra were measured with a 1-nm band-pass in cuvettes with a 0.1-cm pathlength. The signal was averaged for 3 s during wavelength scans and either 5 or 15 s during denaturation experiments. During denaturation experiments, CD spectra were acquired at intervals of 1° C. for (mep-Pro-Gly)$_7$ and 3° C. for (Pro- Mep-Gly)$_7$ and (mep-Mep-Gly)$_7$. At each temperature, solutions were equilibrated for a minimum of 5 min before data acquisition. Values of T$_m$ were determined by fitting molar ellipticity at 225 nm (for (Pro-Mep-Gly)$_7$ and (mep-Mep-Gly)$_7$) or 227 nm (for (mep-Pro-Gly)$_7$) to a two-state model. (See, Becktel, W. J.; Schellman, J. A. *Biopolymers* 1987, 26, 1859-1877). T$_m$ values were determined in triplicate.

Figure 8A:
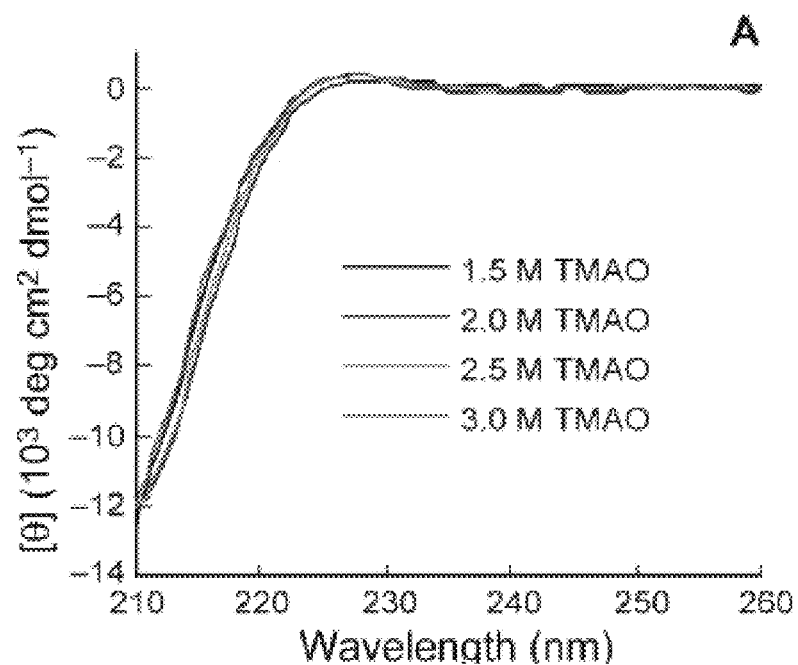
FIGS. 8A-C show circular dichroism spectral data for (mep-Pro-Gly)$_7$. (A) Circular dichroism spectra of (mep-Pro-Gly)$_7$ in the presence of TMAO (1.5, 2.0, 2.5, or 3.0 M) at 4° C. The maxima at ~225 nm are indicative of a collagen triple helix. (B) Thermal denaturation experiments with (mep-Pro-Gly)$_7$ in the presence of TMAO (1.5, 2.0, 2.5, or 3.0 M). Cooperative transitions are apparent in all four solutions. (C) Plot of T$_m$ values for (mep-Pro-Gly)$_7$ versus TMAO concentration. Linear regression and extrapolation to 0 M TMAO gives T$_m$=17.7° C.
Figure 8B:
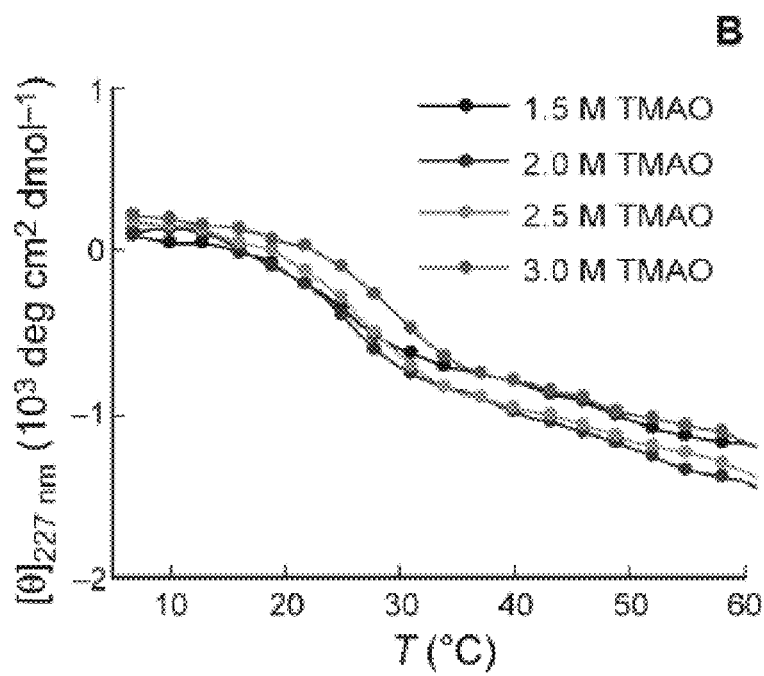
Figure 8C:
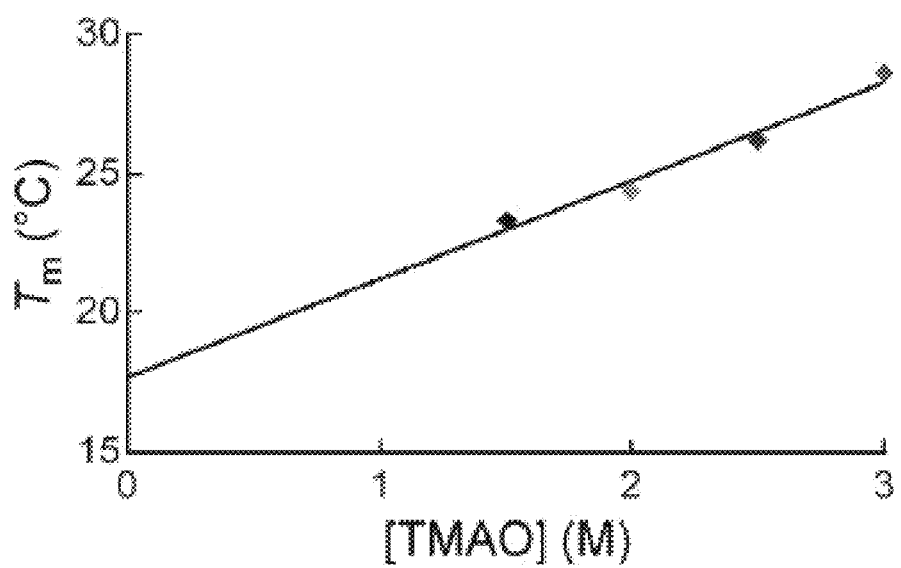

Example 20: Circular Dichroism Spectroscopy of (mep-Pro-Gly)$_7$ in Solutions Containing Trimethylamine-N-Oxide (mep-Pro-Gly)$_7$ was dried under vacuum for 24 h before being weighed and dissolved to 0.2 mM in solutions of 50 mM acetic acid containing 1.5, 2.0, 2.5, or 3.0 M trimethylamine-N-oxide (TMAO), respectively. (Solution pH was corrected to pH=2.9 by addition of concentrated HCl.) Solutions were incubated at ≤4° C. for ≥24 h before CD spectra were recorded using the methods described in the previous section. FIGS. 8A and 8B show the CD spectra and the thermal melts for each solution. The CD spectra show the characteristic maximum at ~227 nm seen for all triple helices, and cooperative transitions were observed during all three thermal melts. FIG. 8C is a plot of T$_m$ values for a (mep-Pro-Gly)$_7$ triple helix versus TMAO concentration. Linear regression and extrapolation to 0 M TMAO predicts a T$_m$ value of 17.7° C. for a (mep-Pro-Gly)$_7$ triple helix, which is similar to the T$_m$ value of 13° C. determined by direct measurement (FIG. 1B and Table 1).

Example 21: Sedimentation Equilibrium Experiments on (mep-Pro-Gly)$_7$, (Pro-Mep-Gly)$_7$, and (mep-Mep-Gly)$_7$ Sedimentation equilibrium experiments were performed with a Beckman XL-A Analytical Ultracentrifuge at the University of Wisconsin Biophysics Instrumentation Facility. Samples were diluted to approximately 0.1 mM in 50 mM potassium phosphate buffer (pH 3) and equilibrated at <4° C. for >24 h. Equilibrium data were collected at multiple speeds at both 4 and 37° C. Gradients were monitored at 230 nm. Solvent densities of 1.00494 and 0.99800 g/mL at 4 and 37° C., respectively, were measured by an Anton Paar DMA5000 density meter. Partial specific volumes ($\bar{v}$) for (mep-Pro-Gly)$_7$, (Pro-Mep-Gly)$_7$ and (mep-Mep-Gly)$_7$ were calculated based on amino acid content and corrected for the monomer molecular weights determined by sedimentation equilibrium experiments at 37° C. A $\bar{v}$ value of 0.781 cm$^3$/g was used for (mep-Pro-Gly)$_7$ and (Pro-Mep-Gly)$_7$ and a $\bar{v}$ value of 0.770 cm$^3$/g was used for (mep-Mep-Gly)$_7$. Data were analyzed with programs written for Igor Pro (Wavemetrics) by Dr. Darrell R. McCaslin (University of Wisconsin Biophysics Instrumentation Facility).

Figure 9:
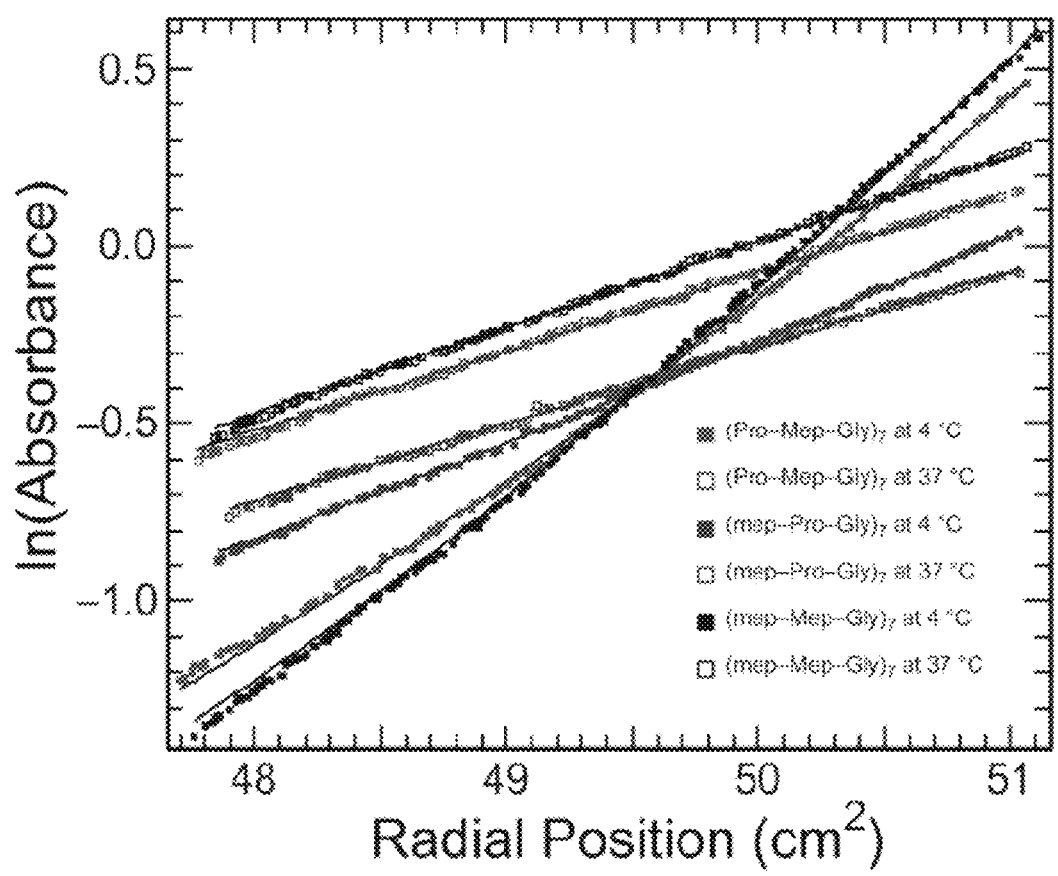
FIG. 9 shows sedimentation equilibrium data. Sedimentation equilibrium data for (Pro-Mep-Gly)$_7$ (red squares), (mep-Pro-Gly)$_7$ (blue squares) and (mep-Mep-Gly)$_7$ (black squares) at a rotor speed of 50,000 rpm. Equilibrium data were collected at 4° C. (filled squares) and 37° C. (open squares). Gradients were monitored at 230 nm. Best fits shown are for solutions containing both trimer and some monomer at 4° C., and for solutions containing only monomer at 37° C.

A log plot of absorbance versus the square of the distance from the center of rotation is shown in FIG. 9. The slope at any point is proportional to the weight-averaged molecular weight, provided that the extinction coefficients per unit mass of assembled and monomeric peptides are equivalent. Curvature in such plots demonstrates the presence of multiple species.

Sedimentation equilibrium results at 37° C. are consistent with a single monomeric species for (mep-Pro-Gly)$_7$, (Pro-Mep-Gly)$_7$, and (mep-Mep-Gly)$_7$, as shown in FIG. 9. At 4° C., the dramatic change in gradient for (Pro-Mep-Gly)$_7$ and (mep-Mep-Gly)$_7$ is consistent with the assembly of these species into a triple helix. The fit shown at 4° C. for these two peptides (FIG. 9) is based on a mixture of monomer and trimer. The data at 4° C. for (mep-Pro-Gly)$_7$ indicates some assembly for this peptide at low temperature, but to a much lesser extent than is observed for the other two peptides. The fit shown in FIG. 9 for (mep-Pro-Gly)$_7$ at 4° C. is for a mixture of monomer and trimer.

Example 22: Computations

The conformational preferences of 4-methylprolines were examined by hybrid density functional theory as implemented in Gaussian 98, Revision A.9, M. J. Frisch, G. et al. Gaussian, Inc., Pittsburgh Pa., 1998. N-Acetyl-4-methylproline methyl esters were used as model compounds in this study. Geometry optimizations and frequency calculations at the B3LYP/6–31+G* level of theory were performed on both the endo and exo conformers of Ac-mep-OMe and Ac-Mep-OMe, which were held in the trans (ω=1800) conformation. Frequency calculations of the optimized structures yielded no imaginary frequencies, indicating a true stationary point on the potential energy surface. Single-point energy calculations at the B3LYP/6–311+G(2d,p) level of theory were performed on the optimized structures. The resulting self-consistent field (SCF) energies were corrected by the zero-point vibrational energy (ZPVE) determined in the frequency calculations, and are listed in FIG. 7.

Example 23: Reciprocity of Steric and Stereoelectronic Effects in the Collagen Triple Helix Density functional theory indicated that the pyrrolidine ring of (2S,4R)-4-methylproline (mep) has a strong preference (1.4 kcal/mol) for the Cγ-endo pucker and that of (2S,4S)-4-methylproline (Mep) has a strong preference (1.7 kcal/mol) for the Cγ-exo pucker. These conformational preferences were observed in crystalline Ac-mep-NHMe and Ac-Mep-NHMe by Flippen-Anderson et al., *J. Am. Chem. Soc.*, 105:6609-6614 (1983), and follow the trend observed in 4-tert-butylprolines by Koskinen et al., *J. Org. Chem.*, 70:6447-6453 (2005). In the preferred conformations, the methyl group of mep and Mep adopts a pseudo-equatorial conformation. A methyl group in this conformation should protrude radially from a collagen triple helix and thus not instill any deleterious steric interactions between the strands of the helix. Accordingly, we synthesized mepOH and MepOH by the method of Del Valle & Goodman, *J. Org. Chem.*, 70:6447-6453 (2005) and incorporated these nonnatural amino acids into collagen strands to yield: (mep-Pro-Gly)$_7$, (Pro-Mep-Gly)$_7$, and (mep-Mep-Gly)$_7$. The incorporation into collagen polymers was performed in the same manner reported in our earlier work in this area, such as U.S. Pat. Nos. 5,973,112 and 7,122,521, both of which are incorporated by reference herein in their entirety. We incubated solutions of each strand at less than or about 4° C., and then used circular dichroism (CD) spectroscopy to detect formation of triple helices and assess their conformational stability. In a similar manner we also made (flp-Mep-Gly)$_7$ and (mep-Flp-Gly)$_7$.

Figure 2:
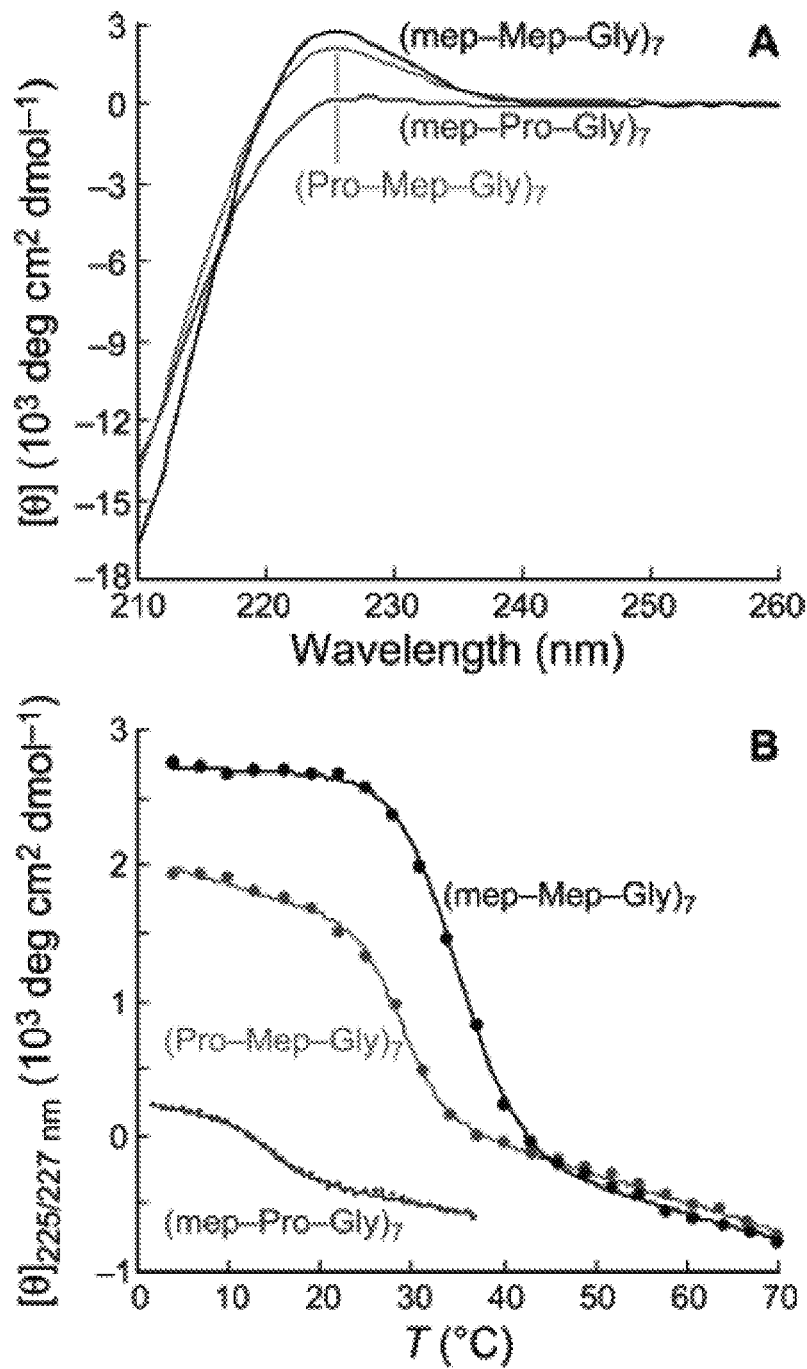
FIG. 2 presents graphical data from the examples below. These data show conformational analysis of (mep-Pro-Gly)$_7$, (Pro-Mep-Gly)$_7$, and (mep-Mep-Gly)$_7$ by CD spectroscopy.

(mep-Pro-Gly)$_7$, (Pro-Mep-Gly)$_7$, and (mep-Mep-Gly)$_7$ formed triple helices at 4° C., as indicated by an ellipiticity maximum near 225 nm (FIG. 2A). The self-association of (Pro-Mep-Gly)$_7$, (mep-Mep-Gly)$_7$, and, to a lesser extent, (mep-Pro-Gly)$_7$ at 4° C. was confirmed by sedimentation equilibrium experiments. (mep-Pro-Gly)$_7$, (Pro-Mep-Gly)$_7$, and (mep-Mep-Gly)$_7$ triple helices had T$_m$ values of 13, 29, and 36° C., respectively, which are much greater than that of (Pro-Pro-Gly)$_7$. The effect of 4-Methylproline and 4-Fluoroproline diastereomers on the conformational stability of the collagen triple helix is shown in Table 1 below. Thus, we conclude that steric effects can indeed stabilize the collagen triple helix. Notably, CD experiments in solutions containing the osmolyte trimethylamine-N-oxide confirm that triple helices of (mep-Pro-Gly)$_7$ have a T$_m$ value near 13° C., but the low molar ellipticity at 227 nm (FIG. 2A) and the results of sedimentation equilibrium experiments suggest that (mep-Pro-Gly)$_7$ is only partially assembled at 4° C.

TABLE 1

| Tripeptide | T$_m$ (±1° C.) | Ref |
|---|---|---|
| (mep-Flp-Gly)$_7$ | 55 | Described herein |
| (flp-Mep-Gly)$_7$ | 51 | Described herein |
| (Pro-Flp-Gly)$_7$ | 45 | J. Am. Chem. Soc. 123, 777-778 (2003) |
| (mep-Mep-Gly)$_7$ | 36 | Described herein |
| (Pro-Hyp-Gly)$_7$ | 36 | J. Am. Chem. Soc. 123, 777-778 (2003) |
| (flp-Pro-Gly)$_7$ | 33 | J. Am. Chem. Soc. 125, 9262-9263 (2003) |
| (Pro-Mep-Gly)$_7$ | 29 | Described herein |
| (mep-Pro-Gly)$_7$ | 13 | Described herein |
| (flp-Flp-Gly)$_7$ | 8$^a$ | J. Am. Chem. Soc. 127, 15923-15932 (2005) |
| (Pro-Pro-Gly)$_7$ | −6$^a$ | J. Am. Chem. Soc. 127, 15923-15932 (2005) |

($^a$Based on the extrapolation of data from solutions containing trimethylamine N-oxide.)

From the data in Table 1, it can be seen that Mep in the Yaa position conferred more stability to a triple helix than does mep in the Xaa position. Likewise, (2S,4R)-4-fluoroproline (Flp) in the Yaa position increased triple-helical propensity more than did (2S,4S)-4-fluoroproline (flp) in the Xaa position. We suspected that this dichotomy could arise from the effect of the steric and stereoelectronic effects on the peptide bond itself.

To determine the effect of a 4-methyl group on the value of K$_{trans/cis}$, we synthesized [$^{13}$CH$_3$]Ac-mep-OMe and [$^{13}$CH$_3$]Ac-Mep-OMe and evaluated K$_{trans/cis}$ with $^{13}$C NMR spectroscopy. The trans:cis ratio was twofold greater for Ac-Mep-OMe (K$_{trans/cis}$=7.4) than for Ac-mep-OMe (K$_{trans/cis}$=3.6). These data provide an explanation for triple helices formed by (Pro-Mep-Gly)$_7$ being more stable than those formed by (mep-Pro-Gly)$_7$. Apparently, a balance exists between preorganization of the proper ring pucker and stabilization of a trans peptide bond.

These findings have numerous implications. Only recently were stereoelectronic effects found to contribute to the conformational stability of a protein. Herein, steric effects are shown to reiterate those same stereoelectronic effects. The stability of a non-natural (mep-Mep-Gly)$_7$ triple helix is indistinguishable from that of the "natural" (Pro-Hyp-Gly)$_7$ triple helix (Table 1), indicating that side-chain heteroatoms (and hence side-chain solvation) are not necessary for the formation of a stable triple helix. The stereoelectronic effects induced by heteroatoms are not additive in collagen. A (flp-Flp-Gly)$_7$ triple helix is less stable than is a (flp-Pro-Gly)$_7$ or (Pro-Flp-Gly)$_7$ triple helix (Table 1), presumably because of an unfavorable steric interaction between fluoro groups on adjacent strands. In contrast, the steric effects are additive, as a (mep-Mep-Gly)$_7$ triple helix is more stable than is a (mep-Pro-Gly)$_7$ or (Pro-Mep-Gly)$_7$ triple helix (Table 1). The methyl groups of mep and Mep in synthetic collagen can likely be elaborated to larger functionalities without undesirable encumbrance. We imagine the creation of a new class of hyperstable collagen mimetics by the judicious integration of stereoelectronic and steric effects. The application of these venerable principles coupled with recent advances in the self-assembly of collagen fragments provides the means to create sturdy synthetic collagens for applications in biomedicine and biotechnology.

The final evidence of the validity of this approach is the synthesis, performed using the procedures described above, of (flp-Mep-Gly)$_7$ and (mep-Flp-Gly)$_7$. These variants were found to have a T$_m$ for (flp-Mep-Gly)$_7$ of 51° C. and a T$_m$ for (mep-Flp-Gly)$_7$ of 55° C., both of which represent a new plateau for collagen mimic stability.

Example 24: Synthesis of N-tert-butyloxycarbonyl-(2S,4R)-4-thioacetyl-proline benzyl ester (16)

Diisopropyl azodicarboxylate (6.29 g, 31.1 mmol) was added dropwise at 0° C. to a solution of triphenyl phosphine (8.16 g, 31.1 mmol) in anhydrous THF (87 mL). The solution was stirred at 0° C. 30 min. A solution of thiolacetic acid (2.36 g, 31.1 mmol) and N-tert-butyloxycarbonyl-(2S, 4S)-hydroxyproline benzyl ester (5.00 g, 15.6 mmol) in anhydrous THF (25 mL) was added dropwise via cannula to the first solution. The reaction mixture was stirred at 0° C. for 1 h, at rt for an additional 1 h and then concentrated under reduced pressure. Flash chromatography (first column: 45% v/v EtOAc in hexane to elute the desired product 16 in a mixture of other byproducts of similar polarity, second column: 6% v/v EtOAc in hexane removed some of the byproducts, and a third column: gradient: 6% v/v EtOAc in hexane to 50% EtOAc in hexane) afforded 16 (3.53 g. 9.6 mmol, 61.5%) as a colorless oil. $^1$H NMR δ: 1.34 and 1.45 (s, 9H), 2.14-2.46 (m, 2H), 2.32 (s, 3H), 3.32 and 3.44 (dd, J=6.4, 10.8, 1H), 3.93 (m, 1H), 4.04 (m, 1H), 4.35 and 4.46 (dd, J=5.1, 8.0, 1H), 5.08-5.29 (m, 2H), 7.35 (m, 5H); $^{13}$C NMR δ: 28.3, 28.5, 30.7, 35.8, 37.1, 39.5, 39.8, 51.6, 52.1, 58.4, 58.7, 67.1, 80.7, 128.2, 128.4, 128.5, 128.6, 128.7, 128.8, 135.5, 135.7, 153.5, 154.1, 172.0, 172.3, 194.8, 194.9; HRMS-ESI (m/z): [M+Na]$^+$ calcd C$_{19}$H$_{25}$NO$_5$SNa, 402.1351; found, 402.1333.

Example 25: Synthesis of N-tert-butyloxycarbonyl-(2S,4R)-4-thioproline (17)

Compound 16 (1.62 g, 4.3 mmol) was dissolved in MeOH (27 mL). 2 N aqueous lithium hydroxide (13.5 mL) was added and the reaction mixture was stirred at rt for 45 min. The reaction mixture was diluted with saturated aqueous NaHCO$_3$ (100 μL) and the MeOH was removed by rotary evaporation. The remaining aqueous solution was washed with ether (3×150 mL), acidified with 2 N aqueous HCl to pH=1, and the acidic aqueous solution was extracted with ether (3×225 mL). The ethereal solution was dried with MgSO$_4$ and concentrated to afford 17 (0.67 g, 63%) as a white solid. $^1$H NMR δ: 1.40-1.68 (2 s, 9H), 1.73 (m, 1H), 2.11-2.79 (m, 2H), 3.41-3.98 (m, 4H), 8.8-9.2 (bs, 1H).

Example 26: Synthesis of N-tert-butyloxycarbonyl-(2S,4R)-4-tritylthio-proline (18)

Compound 17 (0.66 g, 2.7 mmol) was dissolved in DMF (20 mL) and trimethylamine (0.60 g, 5.9 mmol) was added followed by trityl chloride (0.90 g, 3.2 mmol). The reaction mixture was stirred under Ar(g) for 3 h. The DMF was then removed by rotary evaporation under high vacuum. The residue was taken up in 10% w/v aqueous citric acid which was then extracted with ether (100 mL) and ethyl acetate (2×125 mL). The combined organic layers were dried with MgSO₄ and concentrated. Flash chromatography over silica gel in 1:1 v/v EtOAc:hexane afforded 18 (1.53 g, 57%) as a white solid.

Example 27: Synthesis of N-9-Fluorenylmethoxy-carbonyl-(2S,4R)-4-tritylthio-proline (19)

Compound 18 (0.75 g, 1.5 mmol) was dissolved in anhydrous dichloromethane (10 mL) under Ar(g) and the solution was cooled to −15° C. Trifluoroacetic acid (5 mL) was added and the resulting solution was stirred for 4 h, slowly warming to rt over that time period. After concentration, the residue was dissolved in 10% w/v aqueous NaHCO₃ (18 mL) and a solution of Fmoc-OSu (0.57 g, 1.7 mmol) in 1,4-dioxane (25 mL) was added. The resulting solution was stirred for 23 h. The 1,4-dioxane was removed by rotary evaporation and the basic aqueous slurry was acidified with 2 N HCl to pH=1, extracted with EtOAc (3×150 mL), dried with MgSO₄ and concentrated. Flash chromatography over silica gel in 1:3 v/v EtOAc:hexane containing 0.1% formic acid afforded 19 (0.35 g, 35%) as a white solid. ¹H NMR δ: 1.18-1.39 (m, 2H), 1.82-2.14 (m, 1H), 2.81-3.58 (m, 2H), 4.05-4.45 (m, 3H), 7.12-7.79 (m, 23H).

All of the documents cited herein are incorporated by reference here in their entirety).

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

We claim:

1. A collagen mimic comprising a tripeptide having the formula:

(Xaa-Yaa-Gly)n, where Xaa is proline or a trans-4-substituted proline derivative,
where Yaa is proline or a cis-4-substituted proline derivative,
wherein at least one of Xaa, Yaa, or both is the 4-substituted proline derivative, wherein the 4-substituted proline derivative comprises a bulky substituent selected from the group consisting of methyl, ethyl, propyl, isopropyl, and —SH, wherein the substituent is directly installed on C4 of the proline ring, wherein the substituent is electron donating or non-electron withdrawing, and wherein the substituent is capable of stabilizing through steric effects a collagen mimic triple helix wherein one or more strands of the collagen mimic triple helix comprises said collagen mimic, relative to a native collagen triple helix,
and n is a positive integer that is at least 3.

2. The collagen mimic of claim 1, wherein Xaa is a (2S,4R)-4-alkyl proline or a (2S,4R)-4-thioproline, and wherein an electronegative atom including N, O, F, Cl, or Br is not installed directly on C4 of the proline ring.

3. The collagen mimic of claim 2, wherein the (2S,4R)-4-alkyl proline is selected from the group consisting of 4-methylproline, 4-ethylproline, 4-propylproline, 4-isopropylproline, or a longer alkyl proline.

4. The collagen mimic of claim 1, wherein Yaa is a (2S,4S)-4-alkyl proline wherein the 4-alkyl is 4-methyl, 4-ethyl, 4-propyl or 4-isopropyl, or a (2S,4S)-4-thioproline wherein the 4-thio is —SH, and wherein an electronegative atom including N, O, F, Cl, or Br is not installed directly on C4 of the proline ring.

5. The collagen mimic of claim 4, wherein Yaa is the (2S,4S)-4-alkyl proline wherein the 4-alkyl is 4-methyl, 4-ethyl, 4-propyl or 4-isopropyl.

6. The collagen mimic of claim 1, wherein the tripeptide is selected from the group consisting of (Pro-Mep-Gly)n, (mep-Pro-Gly)n, (mep-Mep-Gly)n, (thp-Thp-Gly)n, (thp-Mep-Gly)n, (mep-Thp-Gly)n, (Pro-Thp-Gly)n, and (thp-Pro-Gly)n, where n is a positive integer that is at least 3.

7. A collagen mimic comprising a tripeptide having the formula:

(Xaa-Yaa-Gly)n, where Xaa is proline or proline derivative,
where Yaa is proline or proline derivative,
and further wherein Xaa is (2S,4R)-4-methylproline or Yaa is (2S,4S)-4-methylproline,
and n is a positive integer that is at least 3.

8. A collagen mimic comprising a tripeptide having the formula:

(Xaa-Yaa-Gly)n, where Xaa is proline or proline derivative,
where Yaa is proline or proline derivative,
and further wherein Xaa is (2S,4R)-4-thioproline or Yaa is (2S,4S)-4-thioproline,
and n is a positive integer that is at least 3.

9. The collagen mimic of claim 8, wherein the tripeptide is present in at least one out of every three triplex repeats.

10. A collagen mimic triple helix, wherein one or more strands of the triple helix comprises the collagen mimic of claim 1, wherein through steric effects the collagen mimic triple helix has increased stability relative to a native collagen triple helix.

11. The collagen mimic of claim 10, wherein Xaa is a (2S,4R)-4-alkyl proline or a (2S,4R)-4-thioproline, and wherein an electronegative atom including N, O, F, Cl, or Br is not installed directly on C4 of the proline ring.

12. The collagen mimic of claim 11, wherein the (2S,4R)-4-alkyl proline is selected from the group consisting of 4-methylproline, 4-ethylproline, 4-propylproline, 4-isopropylproline, or a longer alkyl proline.

13. The A collagen mimic triple helix wherein one or more strands of the triple helix comprises the collagen mimic of claim 7, wherein through steric effects the collagen mimic triple helix has increased stability relative to a native collagen triple helix.

* * * * *

UNITED STATES PATENT AND TRADEMARK OFFICE
CERTIFICATE OF CORRECTION

PATENT NO. : 9,758,569 B2
APPLICATION NO. : 11/807270
DATED : September 12, 2017
INVENTOR(S) : Ronald T Raines et al.

It is certified that error appears in the above-identified patent and that said Letters Patent is hereby corrected as shown below:

In the Specification

Column 5, Line 50, "S-proline" should be --(2S)-proline--.

Column 8, Line 43, "S-prolyl-glycine" should be --(2S)-prolyl-glycine--.

Column 8, Line 46, "S-prolyl-gly-" should be --(2S)-prolyl-gly- --.

Column 9, Line 50, "S-prolyl-glycine" should be --(2S)-prolyl-glycine--.

Column 10, Line 6, "S-prolyl-glycine" should be --(2S)-prolyl-glycine--.

In the Claims

Column 20, Claim 13, Line 53, "The A" should be --A--.

Signed and Sealed this
Eleventh Day of September, 2018

Andrei Iancu
*Director of the United States Patent and Trademark Office*